(12) United States Patent
Baroni et al.

(10) Patent No.: US 8,957,211 B2
(45) Date of Patent: Feb. 17, 2015

(54) (HETEROCYCLE/CONDENSED PIPERIDINE)-(PIPERAZINYL)-1-ALKANONE OR (HETEROCYCLE/CONDENSED PYRROLIDINE)-(PIPERAZINYL)-1-ALKANONE DERIVATIVES AND USE THEREOF AS P75 INHIBITORS

(71) Applicant: Sanofi, Paris (FR)

(72) Inventors: Marco Baroni, Vanzago-Milano (IT); Francoise Bono, Toulouse (FR); Sandrine Delbary-Gossart, Mauzac (FR); Valentina Vercesi, Vellezo Bellini (IT)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 14/048,752

(22) Filed: Oct. 8, 2013

(65) Prior Publication Data

US 2014/0038946 A1 Feb. 6, 2014

Related U.S. Application Data

(60) Division of application No. 13/490,904, filed on Jun. 7, 2012, now Pat. No. 8,580,790, which is a continuation of application No. PCT/FR2010/052685, filed on Dec. 13, 2010.

(30) Foreign Application Priority Data

Dec. 14, 2009 (FR) ...................................... 09 06023

(51) Int. Cl.
| | | |
|---|---|---|
| C07D 491/02 | (2006.01) | |
| C07D 498/02 | (2006.01) | |
| C07D 487/08 | (2006.01) | |
| C07D 471/04 | (2006.01) | |
| C07D 495/04 | (2006.01) | |
| C07D 513/04 | (2006.01) | |

(52) U.S. Cl.
CPC ............ *C07D 487/08* (2013.01); *C07D 471/04* (2013.01); *C07D 495/04* (2013.01); *C07D 513/04* (2013.01)
USPC .......... 546/120; 544/2; 544/5; 544/7; 544/10; 544/238; 333/405; 546/113; 546/114; 546/116; 546/122

(58) Field of Classification Search
None
See application file for complete search history.

(56) References Cited

U.S. PATENT DOCUMENTS

| | | | |
|---|---|---|---|
| 7,294,628 B2 | 11/2007 | Bono et al. | |
| 7,423,039 B2 | 9/2008 | Dos Santos et al. | |
| 7,468,368 B2 | 12/2008 | Bono et al. | |
| 7,652,011 B2 | 1/2010 | Bosch et al. | |
| 8,193,190 B2 | 6/2012 | Baroni et al. | |
| 8,518,947 B2 * | 8/2013 | Baroni et al. | ............ 514/252.02 |
| 8,580,790 B2 * | 11/2013 | Baroni et al. | ............ 514/252.02 |
| 2011/0071180 A1 * | 3/2011 | Akireddy et al. | ............ 514/278 |
| 2011/0144122 A1 | 6/2011 | Baroni et al. | |
| 2012/0232280 A1 | 9/2012 | Baroni et al. | |
| 2012/0245150 A1 | 9/2012 | Baroni et al. | |
| 2012/0289518 A1 | 11/2012 | Baroni et al. | |

FOREIGN PATENT DOCUMENTS

| | | |
|---|---|---|
| CN | 1012844838 | 10/2008 |
| CN | 101284838 B * | 5/2011 |
| FR | 2457869 A * | 1/1981 |
| WO | WO 97/28140 A1 | 8/1997 |
| WO | WO 98/17278 | 4/1998 |
| WO | WO 99/01423 A1 | 1/1999 |
| WO | WO 00/51984 A1 | 9/2000 |
| WO | WO 00/59893 A1 | 10/2000 |
| WO | WO 00/69829 | 11/2000 |
| WO | WO 03/104225 A1 | 12/2003 |
| WO | WO 03/104226 A1 | 12/2003 |
| WO | WO 2005/054227 A1 | 6/2005 |
| WO | WO 2005/054229 A1 | 6/2005 |
| WO | WO 2009111550 A1 * | 9/2009 |
| WO | WO 2009/150387 A1 | 12/2009 |

OTHER PUBLICATIONS

CAS RN: 1087792-03-7, Database Chemcats Online, Chemical Abstracts Service, Database Accession No. 0000883057. Order No. T6260461, Enamine Screening Library, (2009).
Della-Bianca, et al., Neurotrophin p75 Receptor is Involved in Neuronal Damage by Prion Peptide-(106-126), The Journal of Biological Chemistry, vol. 276, No. 42. (2001), pp. 38929-38933.
Friedman, et al., Neurotrophin Signaling Via Trks and p75, Experimental Cell Research, vol. 253, pp. 131-142, (1999).
Fukui, et al., Low Affinity NGF Receptor (p75 Neurotrophin Receptor) Inhibitory Antibody Reduces Pain Behavior and CGRP Expression in DRG in the Mouse Sciatic Nerve Crush Model, Journal of Orthopaedic Research, (2010), vol. 28, No. 3, pp. 279-283.
Kendall, et al., p75 Neurotrophin Receptor Signaling Regulates Hepatic Myofibroblast Proliferation and Apoptosis in Recovery From Rodent Liver Fibrosis, Hepatology, (2009), vol. 49, No. 3, pp. 901-910.
Longo, et al., Small Molecule Neurotrophin Receptor Ligands: Novel Strategies for Targeting Alzheimer's Disease Mechanisms, Current Alzheimer Research, (2007), vol. 4, pp. 503-506.
Lowry, et al., A Potential Role for the p75 Low-Affinity Neurotrophin Receptor in Spinal Motor Neuron Degeneration in Murine and Human Amyotrophic Lateral Sclerosis, Amyotroph. Lateral. Scler. (2001), vol. 2, pp. 127-134.

(Continued)

*Primary Examiner* — Alexander R Pagano
(74) *Attorney, Agent, or Firm* — Kelly L. Bender

(57) ABSTRACT

The disclosure relates to (heterocycle-fused piperidine)-(piperazinyl)-1-alkanone derivatives and (heterocycle-fused pyrrolidine)-(piperazinyl)-1-alkanone derivatives of formula (I):

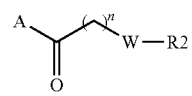

wherein A, W, R2 and n are as defined in the disclosure, to the method of preparation thereof and the therapeutic use thereof.

1 Claim, No Drawings

(56) References Cited

OTHER PUBLICATIONS

Obata, et al., Suppression of the p75 Neurotrophin Receptor in Uninjured Sensory Neurons Reduces Neuropathic Pain After Nerve injury, The Journal of Neuroscience, (2006). vol. 26, No. 46, pp. 11974-11986.

Perlman, et al., Evidence for the Rapid Onset of Apoptosis in Medial Smooth Muscle Cells After Balloon Injury, Circulation, (1997), vol. 95, pp. 981-987.

Rabizadeh, et al., Expression of the Low-Affinity Nerve Growth Factor Receptor Enhances B-Amyloid Peptide Toxicity, Proc. Natl. Acad. Sci. USA, vol. 91, pp. 10703-10706, (1994).

Raychaudhuri, et al., Role of NGF and Neurogenic Inflammation in the Pathogenesis of Psoriasis, Progress in Brain Research, vol. 146, pp. 433-437, (2004).

Rihl, et al., Involvement of Neurotrophins and Their Receptors in Spondyloarthritis Synovitis: Relation to Inflammation and Response to Treatment, Ann Rheum Dis, (2005), vol. 64, pp. 1542-1549.

Roux, et al., P75 Neurotrohpin Receptor Expression is Induced in Apoptotic Neurons After Seizure, The Journal of Neuroscience, (1999), vol. 19, No. 16, pp. 6887-6896.

Saragovi, et al., Small Molecule and Protein-Based Neurotrophic Ligands: Agonists and Antagonists as Therapeutic Agents, Exp. Opin. Ther. Patents, vol. 9(6), pp. 737-751 (1999).

Tokuoka, et al., Disruption of Antigen-Induced Airway Inflammation and Airway Hyper-Responsiveness in Low Affinity Neurotrophin p75 Gene Deficient Mice, British Journal of Pharmacology, (2001), vol. 134, pp. 1580-1586.

Watanabe, et al., The p75 Receptor is Associated With Inflammatory Thermal Hypersensitivity, Journal of Neuroscience Research, vol. 86, pp. 3566-3574, (2008).

Zhu, et al., Up-Regulation of p75 Neurotrophin Receptor (P75NTR) is Associated With Apoptosis in Chronic Pancreatitis, Digestive Diseases and Sciences, vol. 48, No. 4, (2003), pp. 717-725.

CAS RN: 1183620-64-5, 2-Chloro-1-(5,6,7,8-tetrahydro-1,6-naphthyridin-6-yl)ethan-1-one, Database Chemcats (Online), Database Accession No. 2096188618 (2009).

CAS RN: 1179621-56-7, 3-Chloro-1-(5,6,7,8-tetrahydro-1,6-naphthyridin-6-yl)propan-1-one, Database Chemcats (Online), Database Accession No. 2096188619 (2009).

International Search Report for WO2011/080444 dated Jul. 7, 2011.

Chaldakov, G. N., et al., Neurotrophin Presence in Human Coronary Atherosclerosis and Metabolic Syndrome: a Role for NGF and BDNF in Cardiovascular Disease, Progress in Brain Research, vol. 146, pp. 279-289, (2004).

CN 101284838, CAS Abstract AC, 2008:1260833, (2008).

\* cited by examiner

(HETEROCYCLE/CONDENSED PIPERIDINE)-(PIPERAZINYL)-1-ALKANONE OR (HETEROCYCLE/CONDENSED PYRROLIDINE)-(PIPERAZINYL)-1-ALKANONE DERIVATIVES AND USE THEREOF AS P75 INHIBITORS

The subject of the present invention is (heterocycle-fused piperidine)-(piperazinyl)-1-alkanone derivatives and (heterocycle-fused pyrrolidine)-(piperazinyl)-1-alkanone derivatives, the preparation thereof and the therapeutic use thereof.

The compounds according to the present invention have an affinity for the $p75^{NTR}$ neurotrophin receptor.

Neurotrophins belong to a family of proteins of which the biological effect is in particular cell survival and differentiation.

The $p75^{NTR}$ receptor, which is the receptor for all neurotrophins, is a transmembrane glycoprotein of the tumoral necrosis factor (TNF) receptor family (W. J. Friedman and L. A. Greene, Exp. Cell. Res., 1999, 253, 131-142). The $p75^{NTR}$ receptor is expressed in several cell types, and several biological functions have been attributed to said receptor: firstly, modulation of the affinity of neurotrophins for receptor tyrosine kinases (trk); secondly, in the absence of trk, induction of a signal for cell death by apoptosis. Moreover, the neurotrophin precursors, proneurotrophins, are capable of binding to $p75^{NTR}$ with a high affinity, and are considered to be powerful inducers of $p75^{NTR}$-dependent apoptosis in neurons and certain cell lines.

At the level of the central nervous system, many studies show that apoptosis is involved in several pathological conditions, such as amyotrophic lateral sclerosis, multiple sclerosis, Alzheimer's disease, Parkinson's disease, Huntington's disease and prion diseases. $p75^{NTR}$ is also known to be overexpressed in various types of neurodegenerative diseases, such as Alzheimer's disease and amyotrophic lateral sclerosis (ALS) (Longo F. M. et al., Curr. Alzheimer Res. 2007; 4: 503-506; Lowry K. S. et al., Amyotroph. Lateral. Scler. Other. Motor. Neuron. Disord. 2001; 2:127-34).

Results suggest that $p75^{NTR}$ may play a predominant role in the mechanisms resulting in post-ischaemic apoptotic neuron death (P. P. Roux et al., J. Neurosci., 1999, 19, 6887-6896).

Results (V. Della-Bianca et al., J. Biol. Chem., 2001, 276: 38929-33), (S. Rabizadeh et al., Proc. Natl. Acad. Sci. USA, 1994, 91, 10703-10706) support the hypothesis that $p75^{NTR}$ plays an important role in neuron death induced by the infectious prion protein (transmissible spongiform encephalopathy) or by beta-amyloid protein (Alzheimer's disease).

The $p75^{NTR}$ receptor is also associated with the Nogo receptor and involved in the signalling of the inhibitory effects of these myelin proteins with respect to axon growth. As a result, the $p75^{NTR}$ receptor plays a major role in the regulation of neuronal plasticity and in neuron-glia interactions and thus represents a therapeutic target of choice for promoting nerve regeneration.

Beyond the nervous system and neurodegenerative diseases, it has been suggested that $p75^{NTR}$ could play a role in cardiovascular diseases, such as atherosclerosis and myocardial ischaemia (M. L. Bochaton-Pialat et al., Am. J. Pathol., 1995, 146, 1-6; H. Perlman, Circulation, 1997, 95, 981-987). Recent studies show an increase in the expression of $p75^{NTR}$ and of neurotrophins, and massive apoptosis in atherosclerosis lesions.

Several studies also suggest that $p75^{NTR}$ is an inflammation mediator (Rihl M. et al., Ann. Rheum. Dis. 2005; 64 (11): 1542-9; Raychaudhuri S. P. et al., Prog. Brain. Res. 2004; 146: 433-7, Tokuoka S. et al., Br. J. Pharmacol. 2001, 134: 1580-1586).

$p75^{NTR}$ is also described as playing an important role in inflammatory pain. Specifically, nerve damage appears to selectively increase the expression and the axonal transport of $p75^{NTR}$, implicated in the induction of neuropathic pain. Furthermore, the use of a $p75^{NTR}$-specific antibody or of oligodeoxynucleotide antisense capable of blocking the activity of the receptor in vivo appears to be capable of reversing neuropathic pain (heat and cold hyperalgesia and mechanical allodynia) induced in rats after lesion of the L5 spinal nerve (Obata K. et al., J. Neurosci. 2006; 26: 11974-11986). An anti-$p75^{NTR}$ neutralizing antibody considerably reduces inflammatory pain induced by the injection of an adjuvant into the plantar arch in mice, and also in a model of sciatic nerve crush in mice (Watanabe T. et al., J. Neurosci. Res. 2008; 86: 3566-357; Fukui Y. et al. J Orthop Res. 2010; 28(3): 279-83).

The expression of $p75^{NTR}$ is also described in chronic pancreatitis, with implication in the apoptotic process of the exocrine and endocrine pancreas (Zhu Z. et al., Dig. Dis. Sci. 2003; 48 (4): 717-25).

Other reports have also described the importance of $p75^{NTR}$ in the development of hepatic fibrosis (Kendall T. J. et al., Hepatology. 2009; 49 (3): 901-10).

$p75^{NTR}$ also plays an essential role in tumour biology.

Many compounds are known to interact with the trkA/NGF/$p75^{NTR}$ system or to have an NGF-type (nerve growth factor) activity. Thus, patent application WO 00/59893 describes substituted pyrimidine derivatives which have an NGF-type activity and/or which increase the activity of NGF on PC12 cells.

The subject of the present invention is the compounds corresponding to formula (I):

in which:

A represents a group:

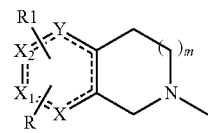

n represents 1 or 2;

m represents 0 or 1;

Y represents a carbon, nitrogen, sulphur or oxygen atom or a single or double bond;

X, $X_1$ and $X_2$ represent a carbon, nitrogen, sulphur or oxygen atom, it being understood that at least one of X, $X_1$ and $X_2$ is other than a carbon atom;

R and R1, located on any one of the available positions, independently represent a hydrogen atom, a halogen atom, a (C1-C4)alkyl group, a (C1-C4)alkoxy group, a perfluoroalkyl radical, a trifluoromethoxy radical, a cyano, or a COOH, COOalkyl, CONR5R6 or NHCOR5 group;

or R1 represents a group chosen from:

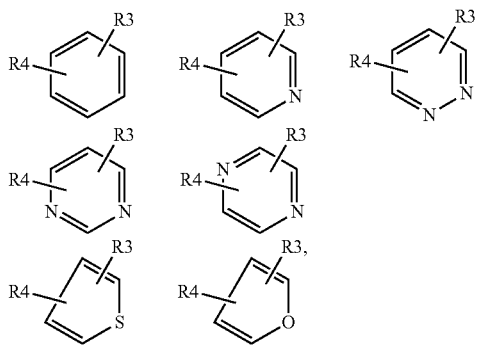

the definition of R remaining unchanged;

R3 and R4, located on any one of the available positions, independently represent a hydrogen atom, a halogen atom, a (C1-C4)alkyl group, a (C1-C4)alkoxy group, a perfluoroalkyl radical, a trifluoromethoxy radical, a cyano, or a COOH, COOalkyl, CONR5R6 or NHCOR5 group;

—W— is a nitrogenous heterocycle chosen from:

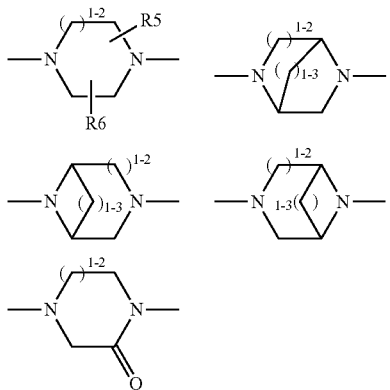

1-2 represents 1 or 2;
1-3 represents 1, 2 or 3;
R2 represents a group of formula:

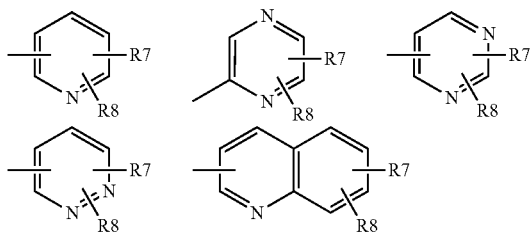

R7 and R8, located on any one of the available positions, independently represent a hydrogen atom, a halogen atom, a (C1-C4)alkyl group, a (C1-C4)alkoxy group, a trifluoromethyl radical, a trifluoromethoxy radical, a cyano, or a COOH, COOalkyl, COOcycloalkyl, SOalkyl, SO₂alkyl, CONH₂, CONR5R6 or NHCOR5 group;

or one of R7 and R8 represents a heterocycle chosen from:

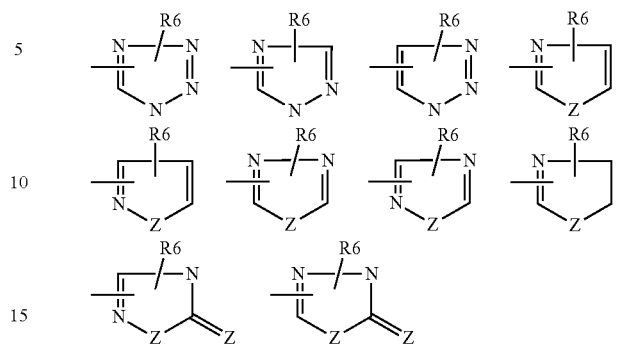

Z represents an oxygen or sulphur atom;
R5 and R6 represent a hydrogen or a C1-C6 alkyl group.

The compounds of formula (I) may comprise one or more asymmetrical carbon atoms. They may therefore exist in the form of enantiomers or diastereoisomers. These enantiomers and diastereoisomers, and also mixtures thereof, including racemic mixtures, form part of the invention.

The compounds of formula (I) may exist in the form of bases or of addition salts with acids. Such addition salts form part of the invention.

These salts may be prepared with pharmaceutically acceptable acids, but the salts of other acids that are useful, for example, for purifying or isolating the compounds of formula (I) also form part of the invention.

In the context of the present invention:
the term "a halogen atom" is intended to mean: a fluorine, a chlorine, a bromine or an iodine;
the term "an alkyl group" is intended to mean: a linear, branched or cyclic, saturated aliphatic group. By way of examples, mention may be made of a C1-C4 alkyl group which may represent a methyl, ethyl, propyl, isopropyl, butyl, isobutyl, tert-butyl, cyclopropyl or cyclobutyl;
the term "a fluoroalkyl group" is intended to mean: an alkyl group of which one or more hydrogen atoms have been substituted with a fluorine atom;
the term "a perfluoroalkyl group" is intended to mean: an alkyl group of which all the hydrogen atoms have been substituted with a fluorine atom, for example a trifluoroalkyl group such as trifluoromethyl;
the term "an alkoxy group" is intended to mean: an —O-alkyl radical where the alkyl group is as defined above;
the term "a perfluoroalkoxy group" is intended to mean: an alkoxy group of which all the hydrogen atoms have been substituted with a fluorine atom, for example a trifluoroalkoxy group such as trifluoromethoxy;
the term "a cycloalkyl group" is intended to mean: a cyclic alkyl group. By way of examples, mention may be made of cyclopropyl, methylcyclopropyl, cyclobutyl, cyclopentyl, cyclohexyl, etc., groups.

Among the compounds of formula (I) which are subjects of the invention, another group of compounds consists of the compounds of formula (I) in which:
n represents 1; and/or
m represents 0 or 1; and/or
Y represents a nitrogen atom, or a single or double bond; and/or
X, $X_1$ and $X_2$ represent a carbon, nitrogen or sulphur atom, it being understood that at least one of X, $X_1$ and $X_2$ is other than a carbon atom; and/or R and R1, located on any one of the available positions, independently represent a hydrogen atom, a halogen atom or a (C1-C4) alkyl group;

or else

R1 represents a group:

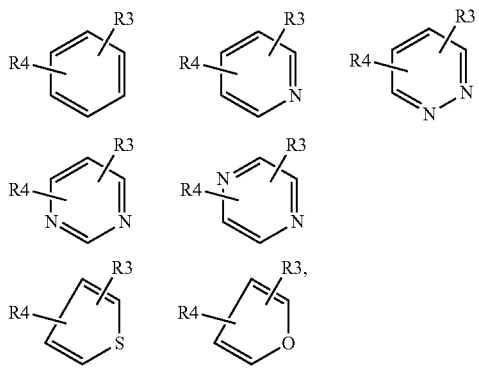

and R is a hydrogen atom; and/or

R3 and R4, located on any one of the available positions, represent a hydrogen atom, a halogen atom, a (C1-C4) alkoxy group or a perfluoroalkyl radical; and/or —W— represents:

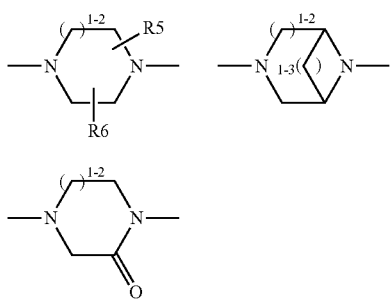

or else

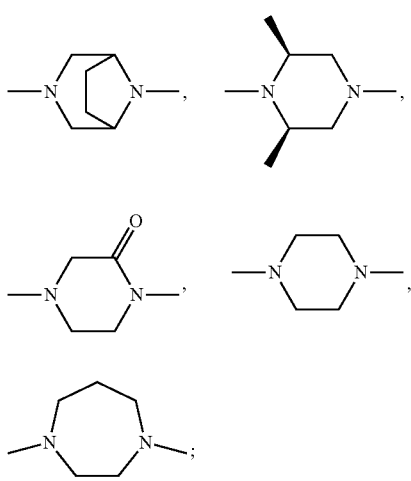

and/or

R2 represents:

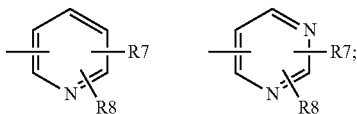

and/or

R7 and R8, located on any one of the available positions, independently represent a hydrogen atom, a halogen atom, a (C1-C4)alkyl group, a trifluoromethyl radical, or a COOH, COOalkyl, SOalkyl or $SO_2$alkyl group; or else one of R7 and R8 represents a heterocycle chosen from:

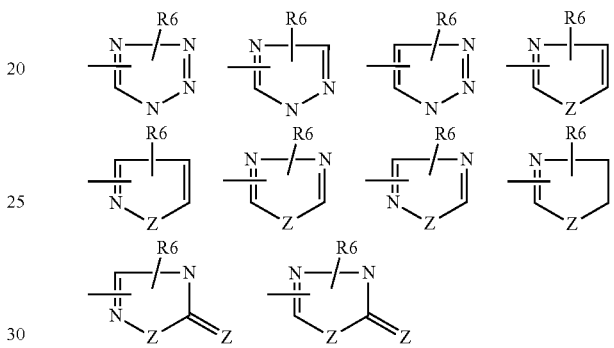

and/or;

R5 and R6 represent a hydrogen atom or a methyl group; in the form of a base or of an addition salt with an acid.

Among the compounds of formula (I) which are subjects of the invention, mention may in particular be made of the following compounds:

Compound No. 1: 1-(6,7-dihydro-4H-thieno[3,2-c]pyridin-5-yl)-2-[8-(5-fluoropyrimidin-2-yl)-3,8-diazabicyclo[3.2.1]oct-3-yl]ethanone;

Compound No. 2: 2-[8-(5-fluoropyrimidin-2-yl)-3,8-diazabicyclo[3.2.1]oct-3-yl]-1-(2-phenyl-6,7-dihydro-4H-thiazolo[5,4-c]pyridin-5-yl)ethanone;

Compound No. 3: 1-(2-chloro-7,8-dihydro-5H-[1,6]naphthyridin-6-yl)-2-[8-(5-fluoropyrimidin-2-yl)-3,8-diazabicyclo[3.2.1]oct-3-yl]ethanone;

Compound No. 4: 2-[8-(5-fluoropyrimidin-2-yl)-3,8-diazabicyclo[3.2.1]oct-3-yl]-1-(2-phenyl-2,4,6,7-tetrahydropyrazolo[4,3-c]pyridin-5-yl)ethanone;

Compound No. 5: 6-{3-[2-oxo-2-(2-phenyl-6,7-dihydro-4H-thiazolo[5,4-c]pyridin-5-yl)ethyl]-3,8-diazabicyclo[3.2.1]oct-8-yl}nicotinic acid methyl ester;

Compound No. 6: 6-{(3S,5R)-3,5-dimethyl-4-[2-oxo-2-(2-phenyl-6,7-dihydro-4H-thiazolo[5,4-c]pyridin-5-yl)ethyl]piperazin-1-yl}nicotinic acid;

Compound No. 7: 6-{3-[2-oxo-2-(2-phenyl-6,7-dihydro-4H-thiazolo[5,4-c]pyridin-5-yl)ethyl]-3,8-diazabicyclo[3.2.1]oct-8-yl}nicotinic acid;

Compound No. 8: 6-{(3S,5R)-3,5-dimethyl-4-[2-oxo-2-(2-phenyl-6,7-dihydro-4H-thiazolo[5,4-c]pyridin-5-yl)ethyl]piperazin-1-yl}nicotinic acid;

Compound No. 9: 2-[(2S,6R)-2,6-dimethyl-4-(5-trifluoromethylpyridin-2-yl)piperazin-1-yl]-1-(2-phenyl-6,7-dihydro-4H-thiazolo[5,4-c]pyridin-5-yl)ethanone;

Compound No. 10: 2-[(2S,6R)-2,6-dimethyl-4-(5-trifluoromethylpyridin-2-yl)piperazin-1-yl]-1-(2-phenyl-2,4,6,7-tetrahydropyrazolo[4,3-c]pyridin-5-yl)ethanone;

Compound No. 11: 4-[2-oxo-2-(2-phenyl-6,7-dihydro-4H-thiazolo[5,4-c]pyridin-5-yl)ethyl]-1-(5-trifluoromethylpyridin-2-yl)piperazin-2-one;

Compound No. 12: 1-(2-phenyl-6,7-dihydro-4H-thiazolo[5,4-c]pyridin-5-yl)-2-[4-(5-trifluoromethylpyridin-2-yl)piperazin-1-yl]ethanone;

Compound No. 13: 1-(2-phenyl-2,4,6,7-tetrahydropyrazolo[4,3-c]pyridin-5-yl)-2-[4-(5-trifluoromethylpyridin-2-yl)piperazin-1-yl]ethanone;

Compound No. 14: 4-[2-oxo-2-(2-phenyl-2,4,6,7-tetrahydropyrazolo[4,3-c]pyridin-5-yl)ethyl]-1-(5-trifluoromethylpyridin-2-yl)piperazin-2-one;

Compound No. 15: 2-[(2S,6R)-4-(5-fluoropyrimidin-2-yl)-2,6-dimethylpiperazin-1-yl]-1-(2-phenyl-6,7-dihydro-4H-thiazolo[5,4-c]pyridin-5-yl)ethanone;

Compound No. 16: 2-((2S,6R)-2,6-dimethyl-4-pyrimidin-5-yl-piperazin-1-yl)-1-(2-phenyl-2,4,6,7-tetrahydropyrazolo[4,3-c]pyridin-5-yl)ethanone;

Compound No. 17: 2-[(2S,6R)-4-(5-fluoropyrimidin-2-yl)-2,6-dimethylpiperazin-1-yl]-1-(2-phenyl-2,4,6,7-tetrahydropyrazolo[4,3-c]pyridin-5-yl)ethanone;

Compound No. 18: 2-[(2S,6R)-2,6-dimethyl-4-(6-trifluoromethylpyridin-3-yl)piperazin-1-yl]-1-(2-phenyl-6,7-dihydro-4H-thiazolo[5,4-c]pyridin-5-yl)ethanone;

Compound No. 19: 6-{3-[2-oxo-2-(2-phenyl-2,4,6,7-tetrahydropyrazolo[4,3-c]pyridin-5-yl)ethyl]-3,8-diazabicyclo[3.2.1]oct-8-yl}nicotinic acid methyl ester;

Compound No. 20: 2-[(2S,6R)-2,6-dimethyl-4-(6-trifluoromethylpyridin-3-yl)piperazin-1-yl]-1-(2-phenyl-2,4,6,7-tetrahydropyrazolo[4,3-c]pyridin-5-yl)ethanone;

Compound No. 21: 6-{(3S,5R)-3,5-dimethyl-4-[2-oxo-2-(2-phenyl-2,4,6,7-tetrahydropyrazolo[4,3-c]pyridin-5-yl)ethyl]piperazin-1-yl}nicotinic acid;

Compound No. 22: 2-((2S,6R)-2,6-dimethyl-4-pyrimidin-5-yl-piperazin-1-yl)-1-(2-phenyl-6,7-dihydro-4H-thiazolo[5,4-c]pyridin-5-yl)ethanone;

Compound No. 23: 6-{(3S,5R)-3,5-dimethyl-4-[2-oxo-2-(2-phenyl-2,4,6,7-tetrahydropyrazolo[4,3-c]pyridin-5-yl)ethyl]piperazin-1-yl}nicotinic acid methyl ester;

Compound No. 24: 6-{3-[2-oxo-2-(2-phenyl-2,4,6,7-tetrahydropyrazolo[4,3-c]pyridin-5-yl)ethyl]-3,8-diazabicyclo[3.2.1]oct-8-yl}nicotinic acid;

Compound No. 25: 6-{2-oxo-4-[2-oxo-2-(2-phenyl-6,7-dihydro-4H-thiazolo[5,4-c]pyridin-5-yl)ethyl]piperazin-1-yl}nicotinic acid methyl ester;

Compound No. 26: 2-[8-(5-fluoropyrimidin-2-yl)-3,8-diazabicyclo[3.2.1]oct-3-yl]-1-(1-phenyl-1,4,6,7-tetrahydropyrazolo[4,3-c]pyridin-5-yl)ethanone;

Compound No. 27: 1-(2-phenyl-2,4,6,7-tetrahydropyrazolo[4,3-c]pyridin-5-yl)-2-(4-pyridin-3-yl[1,4]diazepan-1-yl)ethanone;

Compound No. 28: 1-(2-phenyl-2,4,6,7-tetrahydropyrazolo[4,3-c]pyridin-5-yl)-2-(8-pyridin-3-yl-3,8-diazabicyclo[3.2.1]oct-3-yl)ethanone;

Compound No. 29: 1-(2-phenyl-2,4,6,7-tetrahydropyrazolo[4,3-c]pyridin-5-yl)-2-[8-(5-trifluoromethylpyridin-2-yl)-3,8-diazabicyclo[3.2.1]oct-3-yl]ethanone;

Compound No. 30: 1-(2-phenyl-6,7-dihydro-4H-thiazolo[5,4-c]pyridin-5-yl)-2-(4-pyridin-3-yl-[1,4]diazepan-1-yl)ethanone;

Compound No. 31: 1-(2-phenyl-2,4,6,7-tetrahydropyrazolo[4,3-c]pyridin-5-yl)-2-(8-pyrimidin-5-yl-3,8-diazabicyclo[3.2.1]oct-3-yl)ethanone;

Compound No. 32: 2-[8-(5-fluoropyrimidin-2-yl)-3,8-diazabicyclo[3.2.1]oct-3-yl]-1-(2-methyl-2,4,6,7-tetrahydropyrazolo[4,3-c]pyridin-5-yl)ethanone;

Compound No. 33: 6-{3-[2-oxo-2-(2-phenyl-4,6-dihydropyrrolo[3,4-d]thiazol-5-yl)ethyl]-3,8-diazabicyclo[3.2.1]oct-8-yl}nicotinic acid methyl ester;

Compound No. 34: 4-{2-[2-(4-methoxyphenyl)-6,7-dihydro-4H-thiazolo[5,4-c]pyridin-5-yl]-2-oxoethyl}-1-(5-trifluoromethylpyridin-2-yl)piperazin-2-one;

Compound No. 35: 4-{2-[2-(4-fluorophenyl)-6,7-dihydro-4H-thiazolo[5,4-c]pyridin-5-yl]-2-oxoethyl}-1-(5-trifluoromethylpyridin-2-yl)piperazin-2-one;

Compound No. 36: 2-[8-(5-fluoropyrimidin-2-yl)-3,8-diazabicyclo[3.2.1]oct-3-yl]-1-(2-methyl-6,7-dihydro-4H-thiazolo[5,4-c]pyridin-5-yl)ethanone;

Compound No. 37: 6-(3-{2-[2-(4-methoxyphenyl)-6,7-dihydro-4H-thiazolo[5,4-c]pyridin-5-yl]-2-oxoethyl}-3,8-diazabicyclo[3.2.1]oct-8-yl)nicotinic acid methyl ester;

Compound No. 38: 6-(3-{2-[2-(4-fluorophenyl)-6,7-dihydro-4H-thiazolo[5,4-c]pyridin-5-yl]-2-oxoethyl}-3,8-diazabicyclo[3.2.1]oct-8-yl)nicotinic acid methyl ester;

Compound No. 39: 6-(3-{2-oxo-2-[2-(5-trifluoromethylpyridin-2-yl)-2,4,6,7-tetrahydropyrazolo[4,3-c]pyridin-5-yl]ethyl}-3,8-diazabicyclo[3.2.1]oct-8-yl)nicotinic acid methyl ester;

Compound No. 40: 2-[8-(5-fluoropyrimidin-2-yl)-3,8-diazabicyclo[3.2.1]oct-3-yl]-1-[2-(5-trifluoromethylpyridin-2-yl)-2,4,6,7-tetrahydropyrazolo[4,3-c]pyridin-5-yl]ethanone;

Compound No. 41: 4-[2-oxo-2-(2-phenyl-7,8-dihydro-5H-pyrido[4,3-d]pyrimidin-6-yl)ethyl]-1-(5-trifluoromethylpyridin-2-yl)piperazin-2-one;

Compound No. 42: 4-[2-oxo-2-(2-thiophen-3-yl-6,7-dihydro-4H-thiazolo[5,4-c]pyridin-5-yl)ethyl]-1-(5-trifluoromethylpyridin-2-yl)piperazin-2-one;

Compound No. 43: 2-[8-(5-fluoropyrimidin-2-yl)-3,8-diazabicyclo[3.2.1]oct-3-yl]-1-[2-(4-methoxyphenyl)-2,4,6,7-tetrahydropyrazolo[4,3-c]pyridin-5-yl]ethanone;

Compound No. 44: 6-{3-[2-oxo-2-(2-thiophen-3-yl-6,7-dihydro-4H-thiazolo[5,4-c]pyridin-5-yl)ethyl]-3,8-diazabicyclo[3.2.1]oct-8-yl}nicotinic acid;

Compound No. 45: 2-[8-(5-fluoropyrimidin-2-yl)-3,8-diazabicyclo[3.2.1]oct-3-yl]-1-[1-(2,2,2-trifluoroethyl)-1,4,6,7-tetrahydropyrazolo[4,3-c]pyridin-5-yl]ethanone;

Compound No. 46: 2-[8-(5-fluoropyrimidin-2-yl)-3,8-diazabicyclo[3.2.1]oct-3-yl]-1-[1-(4-methoxyphenyl)-1,4,6,7-tetrahydropyrazolo[4,3-c]pyridin-5-yl]ethanone;

Compound No. 47: 2-[8-(5-fluoropyrimidin-2-yl)-3,8-diazabicyclo[3.2.1]oct-3-yl]-1-(2,4,6,7-tetrahydropyrazolo[4,3-c]pyridin-5-yl)ethanone;

Compound No. 48: 6-{3-[2-oxo-2-(1-phenyl-1,4,6,7-tetrahydropyrazolo[4,3-c]pyridin-5-yl)ethyl]-3,8-diazabicyclo[3.2.1]oct-8-yl}nicotinic acid methyl ester;

Compound No. 49: 6-{3-[2-oxo-2-(1-phenyl-1,4,6,7-tetrahydropyrazolo[4,3-c]pyridin-5-yl)ethyl]-3,8-diazabicyclo[3.2.1]oct-8-yl}nicotinic acid;

Compound No. 50: 1-(1-tert-butyl-1,4,6,7-tetrahydropyrazolo[4,3-c]pyridin-5-yl)-2-[8-(5-fluoropyrimidin-2-yl)-3,8-diazabicyclo[3.2.1]oct-3-yl]ethanone;

Compound No. 51: 1-[1-(4-fluorophenyl)-1,4,6,7-tetrahydropyrazolo[4,3-c]pyridin-5-yl]-2-[8-(5-fluoropyrimidin-2-yl)-3,8-diazabicyclo[3.2.1]oct-3-yl]ethanone;

Compound No. 52: 6-{(2R,5S)-2,5-dimethyl-4-[2-oxo-2-(2-phenyl-2,4,6,7-tetrahydropyrazolo[4,3-c]pyridin-5-yl)ethyl]piperazin-1-yl}nicotinonitrile;

Compound No. 53: 6-{(2R,5S)-2,5-dimethyl-4-[2-oxo-2-(2-phenyl-2,4,6,7-tetrahydropyrazolo[4,3-c]pyridin-5-yl)ethyl]piperazin-1-yl}nicotinic acid;

Compound No. 54: 2-[8-(5-fluoropyrimidin-2-yl)-3,8-diazabicyclo[3.2.1]oct-3-yl]-1-(2-phenyl-4,7-dihydro-5H-furo[2,3-c]pyridin-6-yl)ethanone;

Compound No. 55: 2-[8-(5-fluoropyrimidin-2-yl)-3,8-diazabicyclo[3.2.1]oct-3-yl]-1-(2-phenyl-1,4,5,7-tetrahydropyrrolo[2,3-c]pyridin-6-yl)ethanone;

Compound No. 56: 6-{8-[2-oxo-2-(2-phenyl-6,7-dihydro-4H-thiazolo[5,4-c]pyridin-5-yl)ethyl]-3,8-diazabicyclo[3.2.1]oct-3-yl}nicotinic acid methyl ester;

Compound No. 57: 6-{8-[2-oxo-2-(2-phenyl-2,4,6,7-tetrahydropyrazolo[4,3-c]pyridin-5-yl)ethyl]-3,8-diazabicyclo[3.2.1]oct-3-yl}nicotinic acid methyl ester;

Compound No. 58: 2-[8-(5-fluoropyrimidin-2-yl)-3,8-diazabicyclo[3.2.1]oct-3-yl]-1-(2-phenyl-6,7-dihydro-4H-oxazolo[4,5-c]pyridin-5-yl)ethanone;

Compound No. 59: 6-{(2R,5S)-2,5-dimethyl-4-[2-oxo-2-(2-phenyl-6,7-dihydro-4H-thiazolo[5,4-c]pyridin-5-yl)ethyl]piperazin-1-yl}nicotinonitrile;

Compound No. 60: 2-{8-[5-(5-methyl-[1,2,4]oxadiazol-3-yl)pyridin-2-yl]-3,8-diazabicyclo[3.2.1]oct-3-yl}-1-(2-phenyl-6,7-dihydro-4H-thiazolo[5,4-c]pyridin-5-yl)ethanone;

Compound No. 61: 6-{8-[2-oxo-2-(2-phenyl-2,4,6,7-tetrahydropyrazolo[4,3-c]pyridin-5-yl)ethyl]-3,8-diazabicyclo[3.2.1]oct-3-yl}nicotinic acid;

Compound No. 62: 6-{8-[2-oxo-2-(2-phenyl-6,7-dihydro-4H-thiazolo[5,4-c]pyridin-5-yl)ethyl]-3,8-diazabicyclo[3.2.1]oct-3-yl}nicotinic acid;

Compound No. 63: 6-{(2R,5S)-2,5-dimethyl-4-[2-oxo-2-(2-phenyl-6,7-dihydro-4H-thiazolo[5,4-c]pyridin-5-yl)ethyl]piperazin-1-yl}nicotinic acid;

Compound No. 64: 2-[8-(5-fluoropyrimidin-2-yl)-3,8-diazabicyclo[3.2.1]oct-3-yl]-1-(2-pyridin-4-yl-6,7-dihydro-4H-thiazolo[5,4-c]pyridin-5-yl)ethanone;

Compound No. 65: 4-{2-oxo-2-[2-(5-trifluoromethylpyridin-2-yl)-2,4,6,7-tetrahydropyrazolo[4,3-c]pyridin-5-yl]ethyl}-1-(5-trifluoromethylpyridin-2-yl)piperazin-2-one;

Compound No. 66: 4-{2-oxo-2-[1-(2,2,2-trifluoroethyl)-1,4,6,7-tetrahydropyrazolo[4,3-c]pyridin-5-yl]ethyl}-1-(5-trifluoromethylpyridin-2-yl)piperazin-2-one;

Compound No. 67: 2-[8-(5-fluoropyrimidin-2-yl)-3,8-diazabicyclo[3.2.1]oct-3-yl]-1-(2-phenyl-7,8-dihydro-5H-pyrido[4,3-d]pyrimidin-6-yl)ethanone;

Compound No. 68: 3-(6-{3-[2-oxo-2-(2-phenyl-2,4,6,7-tetrahydropyrazolo[4,3-c]pyridin-5-yl)ethyl]-3,8-diazabicyclo[3.2.1]oct-8-yl}pyridin-3-yl)-4H-[1,2,4]oxadiazol-5-one;

Compound No. 69: 2-[8-(5-fluoropyrimidin-2-yl)-3,8-diazabicyclo[3.2.1]oct-3-yl]-1-(2-phenyl-3,4,6,7-tetrahydroimidazo[4,5-c]pyridin-5-yl)ethanone;

Compound No. 70: 3-(6-{3-[2-oxo-2-(2-phenyl-6,7-dihydro-4H-thiazolo[5,4-c]pyridin-5-yl)ethyl]-3,8-diazabicyclo[3.2.1]oct-8-yl}pyridin-3-yl)-4H-[1,2,4]oxadiazol-5-one;

Compound No. 71: 2-[8-(5-fluoropyrimidin-2-yl)-3,8-diazabicyclo[3.2.1]oct-3-yl]-1-(2-phenyl-6,7-dihydro-4H-thiazolo[4,5-c]pyridin-5-yl)ethanone;

Compound No. 72: 2-{(3S,5R)-3,5-dimethyl-4-[2-oxo-2-(2-phenyl-6,7-dihydro-4H-thiazolo[5,4-c]pyridin-5-yl)ethyl]piperazin-1-yl}pyrimidine-5-carboxylic acid;

Compound No. 73: 2-[8-(5-fluoropyrimidin-2-yl)-3,8-diazabicyclo[3.2.1]oct-3-yl]-1-(2-pyridin-3-yl-6,7-dihydro-4H-thiazolo[5,4-c]pyridin-5-yl)ethanone;

Compound No. 74: 1-(2-phenyl-6,7-dihydro-4H-thiazolo[5,4-c]pyridin-5-yl)-2-{8-[5-(1H-tetrazol-5-yl)pyridin-2-yl]-3,8-diazabicyclo[3.2.1]oct-3-yl}ethanone;

Compound No. 75: 2-{(3S,5R)-3,5-dimethyl-4-[2-oxo-2-(2-phenyl-2,4,6,7-tetrahydropyrazolo[4,3-c]pyridin-5-yl)ethyl]piperazin-1-yl}pyrimidine-5-carboxylic acid;

Compound No. 76: 6-(3-{2-[2-(4-fluorophenyl)-6,7-dihydro-4H-thiazolo[5,4-c]pyridin-5-yl]-2-oxoethyl}-3,8-diazabicyclo[3.2.1]oct-8-yl)nicotinonitrile;

Compound No. 77: 6-{3-[2-oxo-2-(2-phenyl-2,4,6,7-tetrahydropyrazolo[4,3-c]pyridin-5-yl)ethyl]-3,8-diazabicyclo[3.2.1]oct-8-yl}nicotinonitrile;

Compound No. 78: 4-[2-oxo-2-(2-phenyl-3,4,6,7-tetrahydroimidazo[4,5-c]pyridin-5-yl)ethyl]-1-(5-trifluoromethylpyridin-2-yl)piperazin-2-one;

Compound No. 79: 6-{(3S,5R)-3,5-dimethyl-4-[2-oxo-2-(2-phenyl-2,4,6,7-tetrahydropyrazolo[4,3-c]pyridin-5-yl)ethyl]piperazin-1-yl}nicotinic acid ethyl ester;

Compound No. 80: 1-[2-(4-fluorophenyl)-6,7-dihydro-4H-thiazolo[5,4-c]pyridin-5-yl]-2-[8-(5-fluoropyrimidin-2-yl)-3,8-diazabicyclo[3.2.1]oct-3-yl]ethanone;

Compound No. 81: 2-[8-(5-fluoropyrimidin-2-yl)-3,8-diazabicyclo[3.2.1]oct-3-yl]-1-[2-(4-methoxyphenyl)-6,7-dihydro-4H-thiazolo[5,4-c]pyridin-5-yl]ethanone;

Compound No. 82: 4-[2-oxo-2-(2-phenyl-6,7-dihydro-4H-thiazolo[4,5-c]pyridin-5-yl)ethyl]-1-(5-trifluoromethylpyridin-2-yl)piperazin-2-one;

Compound No. 83: 4-[2-oxo-2-(2-phenyl-6,7-dihydro-4H-oxazolo[4,5-c]pyridin-5-yl)ethyl]-1-(5-trifluoromethylpyridin-2-yl)piperazin-2-one;

Compound No. 84: 4-[2-oxo-2-(2-pyridin-3-yl-6,7-dihydro-4H-thiazolo[5,4-c]pyridin-5-yl)ethyl]-1-(5-trifluoromethylpyridin-2-yl)piperazin-2-one;

Compound No. 85: 2-{8-[5-(2-methyl-2H-tetrazol-5-yl)pyridin-2-yl]-3,8-diazabicyclo [3.2.1]oct-3-yl}-1-(2-phenyl-2,4,6,7-tetrahydropyrazolo[4,3-c]pyridin-5-yl)ethanone;

Compound No. 86: 2-{(2S,6R)-2,6-dimethyl-4-[5-(1-methyl-1H-tetrazol-5-yl)pyridin-2-yl]piperazin-1-yl}-1-(2-phenyl-2,4,6,7-tetrahydropyrazolo[4,3-c]pyridin-5-yl)ethanone;

Compound No. 87: 2-{(2S,6R)-2,6-dimethyl-4-[5-(2-methyl-2H-tetrazol-5-yl)pyridin-2-yl]piperazin-1-yl}-1-(2-phenyl-2,4,6,7-tetrahydropyrazolo[4,3-c]pyridin-5-yl)ethanone;

Compound No. 88: 2-[8-(5-fluoropyrimidin-2-yl)-3,8-diazabicyclo[3.2.1]oct-3-yl]-1-[1-(4-trifluoromethylphenyl)-1,4,6,7-tetrahydropyrazolo[4,3-c]pyridin-5-yl]ethanone;

Compound No. 89: 2-{(2S,6R)-2,6-dimethyl-4-[5-(5-methyl[1,2,4]oxadiazol-3-yl)-pyridin-2-yl]piperazin-1-yl}-1-(2-phenyl-2,4,6,7-tetrahydropyrazolo[4,3-c]pyridin-5-yl)ethanone;

Compound No. 90: 2-[(2S,6R)-2,6-dimethyl-4-(5-[1,3,4]oxadiazol-2-ylpyridin-2-yl)piperazin-1-yl]-1-(2-phenyl-2,4,6,7-tetrahydropyrazolo[4,3-c]pyridin-5-yl)ethanone;

Compound No. 91: 2-{(2S,6R)-2,6-dimethyl-4-[5-(3-methyl-[1,2,4]oxadiazol-5-yl)-pyridin-2-yl]piperazin-1-yl}-1-(2-phenyl-2,4,6,7-tetrahydropyrazolo[4,3-c]pyridin-5-yl)ethanone;

Compound No. 92: 6-{(3S,5R)-4-[2-(1-tert-butyl-1,4,6,7-tetrahydropyrazolo[4,3-c]pyridin-5-yl)-2-oxoethyl]-3,5-dimethylpiperazin-1-yl}nicotinic acid methyl ester;

Compound No. 93: 6-{(3S,5R)-4-[2-(1-tert-butyl-1,4,6,7-tetrahydropyrazolo[4,3-c]pyridin-5-yl)-2-oxoethyl]-3,5-dimethylpiperazin-1-yl}nicotinic acid;

Compound No. 94: 6-{3-[2-(1-tert-butyl-1,4,6,7-tetrahydropyrazolo[4,3-c]pyridin-5-yl)-2-oxoethyl]-3,8-diazabicyclo[3.2.1]oct-8-yl}nicotinic acid;

Compound No. 95: 2-[8-(5-fluoropyrimidin-2-yl)-3,8-diazabicyclo[3.2.1]oct-3-yl]-1-(2-phenyl-6,7-dihydro-4H-oxazolo[5,4-c]pyridin-5-yl)ethanone;

Compound No. 96: 4-[2-oxo-2-(2-phenyl-6,7-dihydro-4H-oxazolo[5,4-c]pyridin-5-yl)ethyl]-1-(5-trifluoromethylpyridin-2-yl)piperazin-2-one;

Compound No. 97: 2-[(2S,6R)-2,6-dimethyl-4-(5-trifluoromethylpyridin-2-yl)piperazin-1-yl]-1-(2-phenyl-4,7-dihydro-5H-furano[2,3-c]pyridin-6-yl)ethanone;

Compound No. 98: 6-{(3S,5R)-3,5-dimethyl-4-[2-oxo-2-(2-phenyl-2,4,6,7-tetrahydropyrazolo[4,3-c]pyridin-5-yl)ethyl]piperazin-1-yl}nicotinic acid isopropyl ester;

Compound No. 99: 1-(2-methyl-2,4,6,7-tetrahydropyrazolo[4,3-c]pyridin-5-yl)-2-[8-(5-trifluoromethylpyridin-2-yl)-3,8-diazabicyclo[3.2.1]oct-3-yl]ethanone;

Compound No. 100: 2-[(2S,6R)-2,6-dimethyl-4-(5-trifluoromethylpyridin-2-yl)piperazin-1-yl]-1-(2-methyl-2,4,6,7-tetrahydropyrazolo[4,3-c]pyridin-5-yl)ethanone;

Compound No. 101: 1-(2-phenyl-4,7-dihydro-5H-furano[2,3-c]pyridin-6-yl)-2-[8-(5-trifluoromethylpyridin-2-yl)-3,8-diazabicyclo[3.2.1]oct-3-yl]ethanone;

Compound No. 102: 6-(3-{2-[2-(4-fluorophenyl)-6,7-dihydro-4H-thiazolo[5,4-c]pyridin-5-yl]-2-oxoethyl}-3,8-diazabicyclo[3.2.1]oct-8-yl)nicotinic acid;

Compound No. 103: 2-[(2S,6R)-2,6-dimethyl-4-(5-trifluoromethylpyridin-2-yl)piperazin-1-yl]-1-[2-(5-trifluoromethylpyridin-2-yl)-2,4,6,7-tetrahydropyrazolo[4,3-c]pyridin-5-yl]ethanone;

Compound No. 104: 2-[8-(5-trifluoromethylpyridin-2-yl)-3,8-diazabicyclo[3.2.1]oct-3-yl]-1-[2-(5-trifluoromethylpyridin-2-yl)-2,4,6,7-tetrahydropyrazolo[4,3-c]pyridin-5-yl]ethanone;

Compound No. 105: 6-{(3S,5R)-4-[2-(2-tert-butyl-2,4,6,7-tetrahydropyrazolo[4,3-c]pyridin-5-yl)-2-oxoethyl]-3,5-dimethylpiperazin-1-yl}nicotinic acid;

Compound No. 106: 2-(8-pyridin-3-yl-3,8-diazabicyclo[3.2.1]oct-3-yl)-1-[2-(5-trifluoromethylpyridin-2-yl)-2,4,6,7-tetrahydropyrazolo[4,3-c]pyridin-5-yl]ethanone;

Compound No. 107: 2-[5-(6-trifluoromethylpyridazin-3-yl)-2,5-diazabicyclo[2.2.1]hept-2-yl]-1-[2-(5-trifluoromethylpyridin-2-yl)-2,4,6,7-tetrahydropyrazolo[4,3-c]pyridin-5-yl]ethanone;

Compound No. 108: 2-(6'-chloro-2,3,5,6-tetrahydro[1,2']bipyrazinyl-4-yl)-1-[2-(5-trifluoromethylpyridin-2-yl)-2,4,6,7-tetrahydropyrazolo[4,3-c]pyridin-5-yl]ethanone;

Compound No. 109: 1-(2-phenyl-3,4,6,7-tetrahydroimidazo[4,5-c]pyridin-5-yl)-2-[8-(5-trifluoromethylpyridin-2-yl)-3,8-diazabicyclo[3.2.1]oct-3-yl]ethanone;

Compound No. 110: 2-[(2S,6R)-2,6-dimethyl-4-(5-trifluoromethylpyridin-2-yl)piperazin-1-yl]-1-(2-phenyl-3,4,6,7-tetrahydroimidazo[4,5-c]pyridin-5-yl)ethanone;

Compound No. 111: 2-((3S,5R)-3,5-dimethyl-2,3,5,6-tetrahydro[1,2']bipyrazinyl-4-yl)-1-[2-(5-trifluoromethylpyridin-2-yl)-2,4,6,7-tetrahydropyrazolo[4,3-c]pyridin-5-yl]ethanone;

Compound No. 112: 2-[(2S,6R)-4-(5-chloropyridin-2-yl)-2,6-dimethylpiperazin-1-yl]-1-[2-(5-trifluoromethylpyridin-2-yl)-2,4,6,7-tetrahydropyrazolo[4,3-c]pyridin-5-yl]ethanone;

Compound No. 113: 2-[4-(7-chloroquinolin-4-yl)piperazin-1-yl]-1-(2-phenyl-2,4,6,7-tetrahydropyrazolo[4,3-c]pyridin-5-yl)ethanone;

Compound No. 114: 2-[4-(6-chloropyridin-2-yl)piperazin-1-yl]-1-(2-phenyl-2,4,6,7-tetrahydropyrazolo[4,3-c]pyridin-5-yl)ethanone;

Compound No. 115: 1-(2-pyridin-4-yl-6,7-dihydro-4H-thiazolo[5,4-c]pyridin-5-yl)-2-[8-(5-trifluoromethylpyridin-2-yl)-3,8-diazabicyclo[3.2.1]oct-3-yl]ethanone;

Compound No. 116: 6-{(3S,5R)-3,5-dimethyl-4-[2-oxo-2-(2-phenyl-3,4,6,7-tetrahydroimidazo[4,5-c]pyridin-5-yl)ethyl]piperazin-1-yl}nicotinic acid;

Compound No. 117: 1-(2-pyridin-2-yl-2,4,6,7-tetrahydropyrazolo[4,3-c]pyridin-5-yl)-2-[8-(5-trifluoromethylpyridin-2-yl)-3,8-diazabicyclo[3.2.1]oct-3-yl]ethanone;

Compound No. 118: 2-[(2S,6R)-2,6-dimethyl-4-(5-trifluoromethylpyridin-2-yl)piperazin-1-yl]-1-(2-pyridin-2-yl-2,4,6,7-tetrahydropyrazolo[4,3-c]pyridin-5-yl)ethanone;

Compound No. 119: 4-[2-oxo-2-(2-pyridin-2-yl-2,4,6,7-tetrahydropyrazolo[4,3-c]pyridin-5-yl)ethyl]-1-(5-trifluoromethylpyridin-2-yl)piperazin-2-one;

Compound No. 120: 4-{2-[2-(4-fluorophenyl)-3,4,6,7-tetrahydroimidazo[4,5-c]pyridin-5-yl]-2-oxoethyl}-1-(5-trifluoromethylpyridin-2-yl)piperazin-2-one;

Compound No. 121: 2-(8-pyridin-3-yl-3,8-diazabicyclo[3.2.1]oct-3-yl)-1-(2-pyridin-2-yl-2,4,6,7-tetrahydropyrazolo[4,3-c]pyridin-5-yl)ethanone;

Compound No. 122: 1-[2-(2,2,2-trifluoroethyl)-2,4,6,7-tetrahydropyrazolo[4,3-c]pyridin-5-yl]-2-[8-(5-trifluoromethylpyridin-2-yl)-3,8-diazabicyclo[3.2.1]oct-3-yl]ethanone;

Compound No. 123: 1-[2-(4-fluorophenyl)-3,4,6,7-tetrahydroimidazo[4,5-c]pyridin-5-yl]-2-[8-(5-trifluoromethylpyridin-2-yl)-3,8-diazabicyclo[3.2.1]oct-3-yl]ethanone;

Compound No. 124: 2-[(2S,6R)-2,6-dimethyl-4-(5-trifluoromethylpyridin-2-yl)piperazin-1-yl]-1-[2-(4-fluorophenyl)-3,4,6,7-tetrahydroimidazo[4,5-c]pyridin-5-yl]ethanone;

Compound No. 125: 4-{2-oxo-2-[2-(2,2,2-trifluoroethyl)-2,4,6,7-tetrahydropyrazolo [4,3-c]pyridin-5-yl]ethyl}-1-(5-trifluoromethylpyridin-2-yl)piperazin-2-one;

Compound No. 126: 2-[(2S,6R)-2,6-dimethyl-4-(5-trifluoromethylpyridin-2-yl)piperazin-1-yl]-1-[2-(2,2,2-trifluoroethyl)-2,4,6,7-tetrahydropyrazolo[4,3-c]pyridin-5-yl]ethanone;

Compound No. 127: 1-(2-phenyl-2,4,6,7-tetrahydropyrazolo[4,3-c]pyridin-5-yl)-2-[5-(5-trifluoromethylpyridin-2-yl)-2,5-diazabicyclo[2.2.1]hept-2-yl]ethanone;

Compound No. 128: 6-{3-[2-oxo-2-(2-phenyl-2,4,6,7-tetrahydropyrazolo[4,3-c]pyridin-5-yl)ethyl]-3,8-diazabicyclo[3.2.1]oct-8-yl}nicotinic acid cyclobutyl ester;

Compound No. 129: 2-((2S,6R)-2,6-dimethyl-4-quinolin-2-ylpiperazin-1-yl)-1-(2-phenyl-2,4,6,7-tetrahydropyrazolo[4,3-c]pyridin-5-yl)ethanone;

Compound No. 130: 6-{(3S,5R)-3,5-dimethyl-4-[2-oxo-2-(2-phenyl-2,4,6,7-tetrahydropyrazolo[4,3-c]pyridin-5-yl)ethyl]piperazin-1-yl}nicotinic acid ethyl ester;

Compound No. 131: 2-[(2S,6R)-4-(5-methanesulphonylpyridin-2-yl)-2,6-dimethylpiperazin-1-yl]-1-(2-phenyl-2,4,6,7-tetrahydropyrazolo[4,3-c]pyridin-5-yl)ethanone;

Compound No. 132: 2-[(2S,6R)-4-(5-fluoropyrimidin-2-yl)-2,6-dimethylpiperazin-1-yl]-1-[2-(4-methoxyphenyl)-6,7-dihydro-4H-thiazolo[5,4-c]pyridin-5-yl]ethanone;

Compound No. 133: 1-[2-(4-methoxyphenyl)-6,7-dihydro-4H-thiazolo[5,4-c]pyridin-5-yl]-2-[5-(5-trifluoromethylpyridin-2-yl)-2,5-diazabicyclo[2.2.1]hept-2-yl]ethanone;

Compound No. 134: 1-(2-phenyl-6,7-dihydro-4H-thiazolo[5,4-c]pyridin-5-yl)-2-{4-[5-(2H-pyrazol-3-yl)pyridin-2-yl]piperazin-1-yl}ethanone;

Compound No. 135: 2-[(2S,6R)-2,6-dimethyl-4-(5-thiazol-2-ylpyridin-2-yl)piperazin-1-yl]-1-(2-phenyl-2,4,6,7-tetrahydropyrazolo[4,3-c]pyridin-5-yl)ethanone;

Compound No. 136: 1-(2-phenyl-6,7-dihydro-4H-thiazolo[5,4-c]pyridin-5-yl)-2-[8-(5-thiazol-2-ylpyridin-2-yl)-3,8-diazabicyclo[3.2.1]oct-3-yl]ethanone;

Compound No. 137: 2-[8-(5-[1,2,4]oxadiazol-3-ylpyridin-2-yl)-3,8-diazabicyclo [3.2.1]oct-3-yl]-1-(2-phenyl-2,4,6,7-tetrahydropyrazolo[4,3-c]pyridin-5-yl)ethanone;

Compound No. 138: 1-(2-ethyl-2,4,6,7-tetrahydropyrazolo[4,3-c]pyridin-5-yl)-2-[8-(5-trifluoromethylpyridin-2-yl)-3,8-diazabicyclo[3.2.1]oct-3-yl]ethanone;

Compound No. 139: 2-[(2S,6R)-2,6-dimethyl-4-(5-[1,2,4]oxadiazol-5-ylpyridin-2-yl)piperazin-1-yl]-1-(2-phenyl-2,4,6,7-tetrahydropyrazolo[4,3-c]pyridin-5-yl)ethanone;

Compound No. 140: 6-{(3S,5R)-3,5-dimethyl-4-[2-oxo-2-(2-pyridin-2-yl-2,4,6,7-tetrahydropyrazolo[4,3-c]pyridin-5-yl)ethyl]piperazin-1-yl}nicotinic acid;

Compound No. 141: 2-((2S,6R)-2,6-dimethyl-4-pyridin-3-ylpiperazin-1-yl)-1-(2-pyridin-4-yl-2,4,6,7-tetrahydropyrazolo[4,3-c]pyridin-5-yl)ethanone;

Compound No. 142: 2-((2S,6R)-2,6-dimethyl-4-pyridin-3-ylpiperazin-1-yl)-1-[2-(5-fluoropyridin-2-yl)-2,4,6,7-tetrahydropyrazolo[4,3-c]pyridin-5-yl]ethanone;

Compound No. 143: 2-((2S,6R)-2,6-dimethyl-4-pyridin-3-ylpiperazin-1-yl)-1-[2-(5-trifluoromethylpyridin-2-yl)-2,4,6,7-tetrahydropyrazolo[4,3-c]pyridin-5-yl]ethanone;

Compound No. 144: 6-{(3S,5R)-3,5-dimethyl-4-[2-oxo-2-(2-pyridin-2-yl-2,4,6,7-tetrahydropyrazolo[4,3-c]pyridin-5-yl)ethyl]piperazin-1-yl}nicotinic acid methyl ester;

Compound No. 145: 2-((2S,6R)-2,6-dimethyl-4-pyridin-3-ylpiperazin-1-yl)-1-(2-phenyl-3,4,6,7-tetrahydroimidazo[4,5-c]pyridin-5-yl)ethanone;

Compound No. 146: 2-[(2S,6R)-2,6-dimethyl-4-(5-trifluoromethylpyridin-2-yl)piperazin-1-yl]-1-(2-pyridazin-3-yl-2,4,6,7-tetrahydropyrazolo[4,3-c]pyridin-5-yl)ethanone;

Compound No. 147: 2-[(2S,6R)-2,6-dimethyl-4-(5-trifluoromethylpyridin-2-yl)piperazin-1-yl]-1-(2-ethyl-2,4,6,7-tetrahydropyrazolo[4,3-c]pyridin-5-yl)ethanone;

Compound No. 148: 4-[2-(2-ethyl-2,4,6,7-tetrahydropyrazolo[4,3-c]pyridin-5-yl)-2-oxoethyl]-1-(5-trifluoromethylpyridin-2-yl)piperazin-2-one;

Compound No. 149: 6-{(3S,5R)-3,5-dimethyl-4-[2-oxo-2-(2-phenyl-2,4,6,7-tetrahydropyrazolo[4,3-c]pyridin-5-yl)ethyl]piperazin-1-yl}nicotinic acid;

Compound No. 150: 6-{(3S,5R)-3,5-dimethyl-4-[2-oxo-2-(2-phenyl-2,4,6,7-tetrahydropyrazolo[4,3-c]pyridin-5-yl)ethyl]piperazin-1-yl}nicotinic acid;

in the form of a base or of an addition salt with an acid.

In the subsequent text, the term "protective group Pg" is intended to mean a group which makes it possible, firstly, to protect a reactive function such as a hydroxyl or an amine during a synthesis and, secondly, to regenerate the intact reactive function at the end of synthesis. Examples of protective groups and also methods of protection and of deprotection are given in *Protective Groups in Organic Synthesis*, Green et al., 2nd Edition (John Wiley & Sons, Inc., New York).

In accordance with the invention, the compounds of general formula (I) are prepared according to the process which follows.

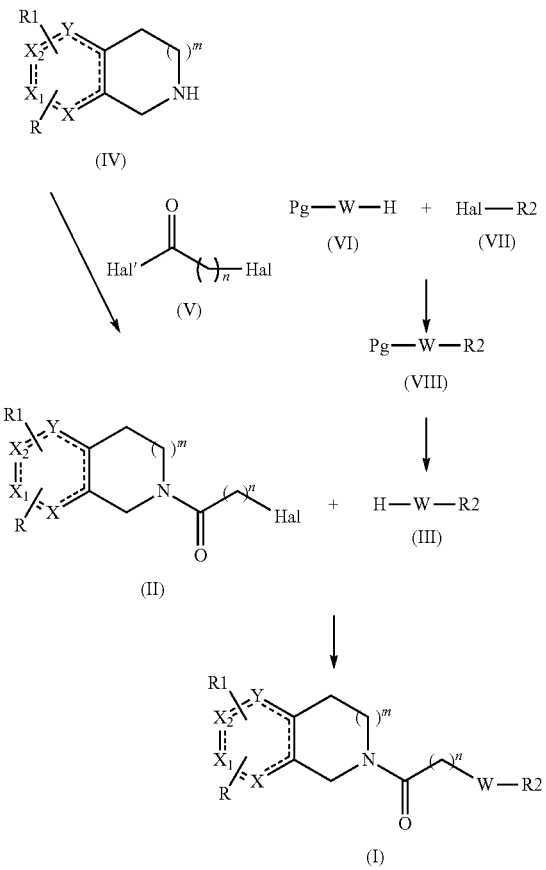

More specifically, the process for preparing the compounds of general formula (I) in which R, R1, X, X1, X2, Y, W, R2, m and n are as defined above comprises the reaction of a compound of formula (II):

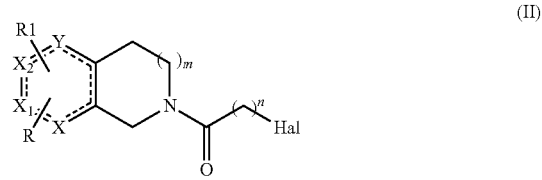

in which R, R1, X, X1, X2, Y, m and n are defined as in general formula (I) and Hal represents a halogen atom, for example chlorine; and of a compound of general formula (III):

in which W and R2 are defined as in general formula (I), according to methods known to those skilled in the art, for example in the presence of a base, in a solvent as described in WO 03/104225. Thus, by way of base, mention may be made of organic bases such as triethylamine, N,N-diisopropylamine, diisopropylethylamine (DPEA) or N-methylmorpholine or alkali metal carbonates or bicarbonates such as potassium carbonate, sodium carbonate or sodium bicarbonate and in the absence or in the presence of an alkali metal iodide such as potassium iodide or sodium iodide. The reaction is carried out in a solvent such as acetonitrile, N,N-dimethylformamide (DMF), N-methylpyrrolidinone, toluene or propan-2-ol, and at a temperature between ambient temperature and the reflux temperature of the solvent. The "ambient temperature" is intended to mean a temperature between 5 and 25° C. By way of example, the reaction can be carried out in the presence of sodium bicarbonate and of sodium iodide in a solvent such as DMF. These reactions can also be carried out in a microwave reactor.

In the compounds of general formula (I) thus obtained, R, R1, R3, R4, R5, R6, R7 and R8 can be modified by treatments commonly used by those skilled in the art, for instance by hydrolysis of an ester group so as to give a carboxylic group or of a cyano so as to obtain a tetrazole group.

Generally, the acid addition salts of the compounds of general formula (I) can be obtained by addition of the appropriate acid, such as hydrochloric acid, hydrobromic acid or oxalic acid.

The compounds of formula (III), optionally in the form of salts, can be prepared from the corresponding compounds of the formula (VIII):

Pg-W—R2        (VIII)

in which W and R2 are as defined in formula (I) and Pg represents a protective group for a nitrogen atom of W. Preferably, Pg is a benzyl group and the deprotection is carried out according to conventional methods well known to those skilled in the art, for example by catalytic hydrogenation on Pd/C or by treatment with chloroformates followed by hydrolysis in an acid medium.

The compounds of formula (VIII) can be prepared from the compounds of formula (VI):

Pg-W—H        (VI)

and (VII):

Hal-R2        (VII)

in which Pg, W and R2 are defined as above and Hal represents a halogen atom, preferably chlorine. This reaction is generally carried out under the same conditions as the reaction for preparing the compounds of formula (I) from the compounds of formulae (II) and (III).

Alternatively, the compounds of formula (VIII) can be prepared by the Buchwald coupling method in the presence of a palladium catalyst and of an opportunely chosen phosphine, using, as solvent, inert solvents such as toluene or xylene, at a temperature between ambient temperature and 110° C.

In the compounds of general formula (VIII) thus obtained, R7 and R8 can be modified by treatments commonly used by those skilled in the art, for instance the synthesis of an oxadiazole group from a cyano group, or else by Suzuki couplings as described in the scheme below.

In Scheme 2 above, L represents a leaving group such as iodo, bromo or trifluoromethanesulphonate; R7 represents a heterocycle as described in general formula (I), R8 is as defined in general formula (I) and B represents a boron atom.

Examples of such reactions are described in the experimental section.

The compounds of formula (III), optionally in the form of salts, when W represents an oxopiperazine, are commercially available or described in the literature, or else can be prepared, from the corresponding compounds of formula (VII), according to methods which are described or known to those skilled in the art.

Examples of such preparations are described in the experimental section.

The compounds of formula (II) can be obtained by reaction of a corresponding compound of formula (IV):

in which R, R1, X, X1, X2, Y and m are defined as in general formula (I), optionally in the form of an acid addition salt, and of a compound of formula (V):

in which Hal and n are as defined in formula (II) and Hal' represents a halogen atom, which may be identical to or different from Hal. Preferably, Hal' represents a chlorine atom.

This reaction is generally carried out in the presence of a base, such as triethylamine, N,N-diisopropylethylamine or N-methylmorpholine, in a solvent such as dichloromethane, chloroform, tetrahydrofuran, dioxane or a mixture of these solvents, and at a temperature between 0° C. and ambient temperature. The compounds of formula (V) are generally commercially available.

Scheme 2

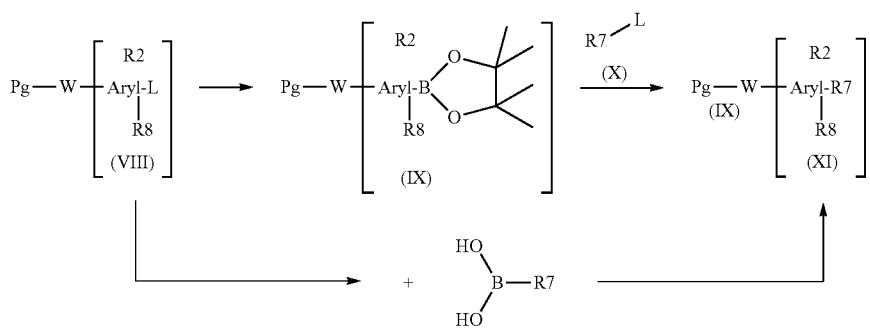

Optionally, the process according to the invention comprises the subsequent step consisting in isolating the desired product obtained.

The products of formulae (IV), (V), (VI) and (VII), and the reactants, when their method of preparation is not described, are commercially available or described in the literature, or else can be prepared according to methods which are described or known to those skilled in the art.

Alternatively, the compounds of formula (I) can be prepared according to Scheme 3 which follows:

triethylamine, N,N-diisopropylamine or diisopropylethylamine (DPEA) and of a condensation agent such as BOP, DBU or DCC. The reaction is carried out at a temperature between ambient temperature and the reflux temperature of the solvent. The term "ambient temperature" is intended to mean a temperature between 5 and 25° C. By way of example, the reaction can be carried out in the presence of sodium bicarbonate, of sodium iodide, in a solvent such as DMF. These reactions can also be carried out in a microwave reactor.

Scheme 3

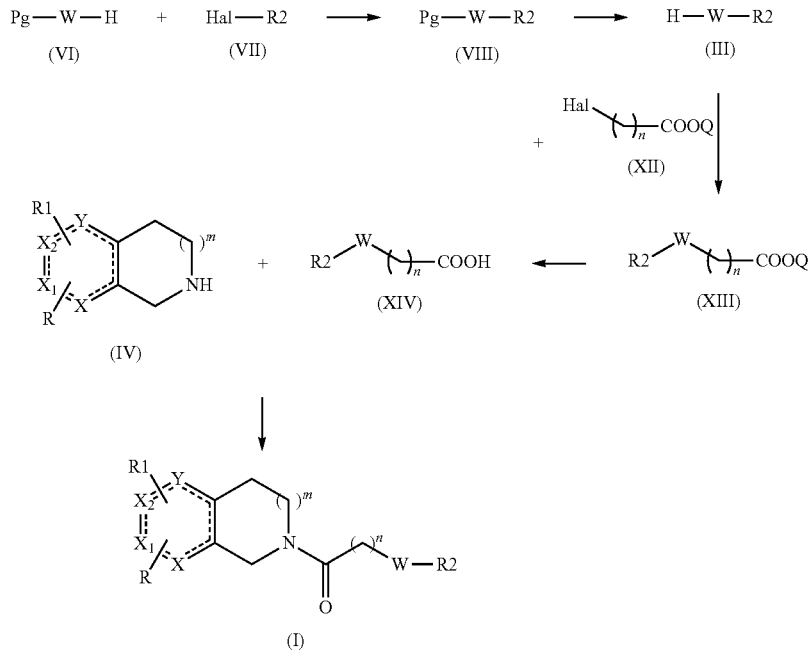

More specifically, the process for preparing the compounds of general formula (I) in which R, R1, X, X1, X2, Y, W, R2, m and n are as defined above and Q represents a residue capable of forming an ester, such as methyl, ethyl or benzyl, comprises the reaction of a compound of formula (XIV):

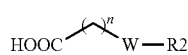
(XIV)

in which R2, W and n are defined as in general formula (I) and of a compound of general formula (IV)

(IV)

in which R, R1, X, X1, X2, Y and m are defined as in general formula (I), according to methods known to those skilled in the art, for example, in a solvent such as dichloromethane, DMF or THF, in the presence of a base such as pyridine, In the compounds of general formula (I) thus obtained, R, R1, R3, R4, R5, R6, R7 and R8 can be modified by treatments commonly used by those skilled in the art, for example by hydrolysis of an ester group so as to give a carboxylic group or of a cyano so as to give a tetrazole group.

Generally, the acid addition salts of the compounds of general formula (I) can be obtained by addition of the appropriate acid, such as hydrochloric acid, hydrobromic acid or oxalic acid.

The compounds of formula (XIV) can be obtained from compounds of formula (XIII)

(XIII)

in which R2, W and n are defined as in general formula (I) and Q represents a residue capable of forming an ester, such as methyl, ethyl or benzyl, by hydrolysis of the ester bond according to methods known to those skilled in the art, for example by a treatment in an acidic or basic aqueous medium, or else by reduction in a polar solvent such as an alcohol or THF, under a hydrogen stream.

The compounds of formula (XIII) can be obtained from compounds of formula (III)

(III)

in which R2 and W are defined as in general formula (I); optionally in the form of an acid addition salt, and from a compound of formula (XII):

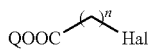

(XII)

in which Q represents a residue capable of forming an ester such as methyl, ethyl or benzyl. Hal represents a halogen atom, preferably a chlorine atom, n is as defined in general formula (I).

This reaction is generally carried out in the presence of a base, such as triethylamine, N,N-diisopropylethylamine or N-methylmorpholine, in a solvent such as dichloromethane, chloroform, tetrahydrofuran, dioxane or a mixture of these solvents, and at a temperature between 0° C. and ambient temperature. The compounds of formula (XII) are generally commercially available.

The compounds of formula (III), optionally in the form of salts, can be prepared from the corresponding compounds of formula (VIII):

Pg-W—R2    (VIII)

in which W and R2 are as defined in formula (I) and Pg represents a protective group for a nitrogen atom of W. Preferably, Pg is a benzyl group and the deprotection is carried out according to conventional methods known to those skilled in the art, for example by catalytic hydrogenation on Pd/C or by treatment with chloroformates followed by hydrolysis in an acid medium.

The compounds of formula (VIII) can be prepared from the compounds of formula (VI):

Pg-W—H    (VI)

and (VII):

Hal-R2    (VII)

in which Pg, W and R2 are defined as above and Hal represents a halogen atom, preferably chlorine. This reaction is generally carried out under the same conditions as in the reaction for preparing the compounds of formula (I) from the compounds of formulae (IV) and (XIV).

Alternatively, the compounds of formula (VIII) can be prepared by the Buchwald coupling method in the presence of a palladium catalyst and of an opportunely chosen phosphine, using, as solvent, inert solvents such as toluene or xylene, at a temperature between ambient temperature and 110° C.

In the compounds of general formula (VIII) thus obtained, R7 and R8 can be modified by treatments commonly used by those skilled in the art, for instance the synthesis of an oxadiazole group from a cyano group, or else by Suzuki couplings as already described in Scheme 2 already set out above.

The compounds of formula (III), optionally in the form of salts, where W represents an oxopiperazine, are commercially available or described in the literature, or else can be prepared, from the corresponding compounds of formula (VII), according to methods which are described or known to those skilled in the art.

Examples of such preparations are described in the experimental section.

Optionally, the process according to the invention comprises the subsequent step consisting in isolating the desired product obtained.

The products of formulae (IV), (VI) and (VII), and the reactants, when their method of preparation is not described, are commercially available or described in the literature, or else can be prepared according to methods which are described or known to those skilled in the art.

Examples of such preparations are described in the experimental section.

According to another of its aspects, a subject of the invention is also compounds of formula (II)

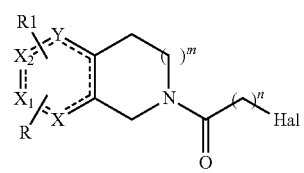

(II)

in which R1, R, X, X1, X2, Y, m, n and Hal are defined as above; in the form of a base or of an addition salt with an acid. These compounds are of use as synthesis intermediates for the compounds of formula (I).

The following examples describe the preparation of certain compounds in accordance with the invention. These examples are not limiting and merely illustrate the present invention. The numbers of the compounds exemplified refer back to those as were given in the table hereinafter, which illustrates the chemical structures and the physical properties of some compounds according to the invention.

The physicochemical measurements were carried out in the following way:

The melting points were measured with a Buchi B540 instrument.

The proton nuclear magnetic resonance (1H NMR) spectra were recorded under the following conditions:

a) at 500 MHz on a Bruker instrument equipped with an Avance III console;

b) at 400 MHz on a Bruker instrument equipped with an Avance I console.

The chemical shifts are reported in ppm relative to the TMS frequency.

The spectra were recorded under the following temperature conditions:

Temp. A: 40° C.

Temp. B: 30° C.

The abbreviations used to characterize the signals are the following: s=singlet, bs=broad singlet, m=multiplet, bm=broad multiplet, d=doublet, bd=broad doublet, t=triplet, q=quadruplet.

*=not integratable because of interference with a broad peak due to water.

**=not integratable because of interference with a peak due to the NMR solvent.

2Xs=two partially superimposed singlets.

2Xbs=two partially superimposed broad singlets.

2Xm=two partially superimposed multiplets.

The HPLC was carried out by means of a ThermoElectron LCQ Deca XP Max system equipped with an ion trap mass spectrometry detector and a diode array detector.

The conditions for analysis by liquid chromatography coupled to mass spectrometry (LC/UV/MS) are the following:

Chromatographic System A

Eluent A=$H_2O$+0.01% TFA

Eluent B=$CH_3CN$

Gradient of 98% of A to 95% of B in 10 minutes, then elution with 95% of B for 5 minutes.
Flow rate 0.5 ml/minute; temperature 40° C.
Injection of 2 μl of solution at 0.1 mg/ml in a mixture of $CH_3CN:H_2O=9:1$
Chromatographic System B
Eluent A=$H_2O$+0.05% TFA
Eluent B=$CH_3CN$+0.035% TFA
Gradient of 98% of A to 95% of B in 12 minutes, then elution with 95% of B for 3 minutes
Flow rate 0.7 ml/minute; temperature 40° C.
Injection of 2 μl of solution at 0.1 mg/ml in a mixture of $CH_3CN:H_2O=9:1$
Chromatographic System C
Eluent A=5 mM ammonium acetate buffer, pH 6.5
Eluent B=$CH_3CN$
Gradient of 98% of A to 95% of B in 10 minutes, then elution with 95% of B for 5 minutes.
Flow rate 0.5 ml/minute; temperature 40° C.
Injection of 2 μl of solution at 0.1 mg/ml in a mixture of $CH_3CN:H_2O=9:1$.
The products are detected by UV at 220 nm.
The columns used are C18 columns with a particle size between 2 and 5 μm, preferably 3.5 μm.
For the mass spectrometry part:
Ionization mode: positive electrospray (ESI+)
Scanning from 100 to 1200 uma.
The thin-layer chromatography was carried out on Merck Silica gel 60 TLC plates. The silica gel for flash column chromatography is sold by Biotage or Supelco.
All the solvents used are of "reagent grade" or "HPLC grade" purity.

Preparation 1

(3R,5S)-3,5-Dimethyl-1-(5-trifluoromethylpyridin-2-yl)piperazine 0.8 g of 2-chloro-5-(trifluoromethyl)pyridine (compound of formula (VII)), 0.5 g of cis-2,6-dimethylaminopiperazine (compound of formula (VI)), 0.67 g of potassium carbonate and 0.3 g of NaI are charged to 8 ml of DMF. The reaction is carried out in a CEM discover microwave initiator for 30 min at 160° C. The resulting product is then poured into a saturated aqueous solution of sodium chloride and the resulting mixture is extracted with ethyl acetate. The organic phase is dried over $Na_2SO_4$, filtered and evaporated under vacuum. 1.1 g of an oily material corresponding to the title product are obtained.

Preparation 2

2-[8-(5-Fluoropyrimidin-2-yl)-3,8-diazabicyclo[3.2.1]octane hydrochloride 1.44 g of 2-chloro-5-fluoropyrimidine (compound of formula (VII)), 2.2 g of 1-benzyl-3,8-diazabicyclo[3.2.1]octane (compound of formula (VI)), 1.7 g of potassium carbonate and 0.73 g of NaI are charged to 27 ml of N-methylpyrrolidone. The mixture is heated at 110° C. for 5 hours. The resulting product is then poured into a saturated aqueous solution of sodium chloride and the resulting mixture is extracted with ethyl acetate. The organic phase is dried over $Na_2SO_4$, filtered and evaporated under vacuum. 3.2 g of an oily material are isolated, and purified by flash chromatography on a Biotage® column, elution being carried out with 95 cyclohexane/5 ethyl acetate. 1.4 g of white solid are isolated, and dissolved in 35 ml of 1,2-dichloroethane. 0.72 ml of 1-chloroethyl chloroformate is added at 0° C. and the mixture is left to stir under a nitrogen stream for 10 minutes at 0° C. and then 3 hours at 85° C. The solvent is evaporated off and 35 ml of methanol are added. Heating is carried out for 30 minutes at the reflux temperature. The solvent is evaporated off and the residue is treated with isopropanol. A white solid is obtained, which is filtered, and 900 mg of title product are isolated. Mp 236-239° C.

Preparation 3

(3R,5S)-3,5-Dimethyl-1-(6-trifluoromethylpyridin-2-yl)piperazine 2.2 g of 2-trifluoromethyl-6-bromopyridine (compound of formula (VII)), 1.1 g of cis-2,6-dimethylpiperazine (compound of formula (VI)), 0.22 g of palladium acetate, 0.28 g of sodium t-butoxide and 1.3 g of tri-t-butyl phosphine are charged to 16 ml of o-xylene. Heating is carried out at 120° C. for 6 hours. The resulting product is filtered through celite and the solvent is evaporated off. 1.8 g of an oily material corresponding to the title product are isolated.

Preparation 4

3,8-Diazabicyclo[3.2.1]oct-8-ylnicotinic acid methyl ester hydrochloride 0.42 g of methyl 6-chloronicotinate (compound of formula (VII)), 0.5 g of 1-benzyl-3,8-diazabicyclo[3.2.1]octane (compound of formula (VI)), 0.4 g of potassium carbonate and 0.17 g of NaI are charged to 7 ml of N-methylpyrrolidone. Heating is carried out for 7 hours at 110° C. The resulting product is then poured into a saturated aqueous solution of sodium chloride and the resulting mixture is extracted with ethyl acetate. The organic phase is dried over $Na_2SO_4$, filtered and evaporated under vacuum. 1.1 g of an oily material are obtained, and purified by flash chromatography on a Biotage® column, elution being carried out with 8 cyclohexane/2 ethyl acetate. 520 mg of a light oil are isolated. The product obtained in the preceding step is hydrogenated at 40° C. under atmospheric pressure for 2 hours in 20 ml of ethanol and 2 ml of isopropanol.HCl, in the presence of 0.22 g of Pd/C at 10%. Filtration is performed, evaporation is carried out under vacuum, and 440 mg of the title product are isolated in the form of a white solid.

Preparation 5

6-(2-Oxopiperazin-1-yl)nicotinic acid methyl ester hydrochloride

Step a) 6-(2-Benzylaminoethylamino)nicotinic acid methyl ester 4.6 g of methyl 6-chloronicotinate and 40.5 ml of N-benzylethylenediamine are heated at 135° C. for 6 hours in a round-bottomed flask. The resulting product is poured into water and extraction is carried out with ethyl acetate. The resulting product is dried and evaporated under vacuum; the crude product thus obtained is purified by flash chromatography.

Step b) 6-(4-Benzyl-2-oxopiperazin-1-yl)nicotinic acid methyl ester

The product of step a), 2.2 g, is solubilized in 35 ml of a 2N solution of HCl. 5 g of trimeric glyoxal dihydrate are added and the mixture is left to stir at ambient temperature for 120 hours. Extraction is carried out with ethyl acetate. The resulting product is dried and evaporated under vacuum; the crude product thus obtained is purified by flash chromatography.

Step c) (6-(2-Oxopiperazin-1-yl)nicotinic acid methyl ester hydrochloride)

The isolated product of 1.4 g is solubilized in 150 ml of ethanol and then 4 ml of a solution of isopropanol saturated with HCl and 0.6 g of Pd/C at 10% are added. The mixture is left to react under a hydrogen stream for 4 hours at a temperature of 40° C. Filtration is performed, and evaporation under vacuum is carried out, and 0.52 g of the title compound is obtained.

Preparation 6

2-Chloro-1-(2-phenyl-6,7-dihydro-4H-thiazolo[4,5-c]pyridin-5-yl)ethanone

Step a) (2-Bromo-4-piperidone)

10 g of 1-Boc-4-piperidone are dissolved in 280 ml of dichloromethane. 8 g of bromine are slowly added and the mixture is left to stir at ambient temperature for 2 hours. Evaporation is carried out under vacuum and a solid is obtained. It is treated with isopropyl ether so as to obtain a white solid which is filtered.

Step b) (2-Phenyl-4,5,6,7-tetrahydrothiazolo[5,4-c]pyridine)

4.5 g of the product of step a) are charged to a round-bottomed flask with 34 ml of DMF and 2.6 g of thiobenzamide. Heating is carried out at a temperature of 60° C. for 6 hours. An aqueous ammonia solution is added until a basic pH is obtained and evaporation is carried out under vacuum. Purification is carried out on a column by flash chromatography by means of a Biotage® column which is eluted with ethyl acetate and then with methanol. 4 g of a brown solid are isolated, and crystallized with isopropanol. Filtration is carried out and 2.8 g of a beige solid are obtained.

Step c) (2-Chloro-1-(2-phenyl-6,7-dihydro-4H-thiazolo[4,5-c]pyridin-5-yl)ethanone)

In a round-bottomed flask with a magnetic stirrer, 2.8 g of this product are suspended in 50 ml of dichloromethane. 2.8 ml of triethylamine are added and the mixture is brought to 0° C. At 0° C., 1.5 ml of chloroacetyl chloride, i.e. the compound of general formula (V) in which Hal=Hal'=Cl and n=1, are run in dropwise. The mixture is left to react for 1 and a half hours and poured into water. Extraction is carried out with dichloromethane. The organic phase is dried over $Na_2SO_4$, filtered and evaporated under vacuum. 4.1 g of a dark oily fat are isolated, triturated, and then left to stand in the cold. The resulting product is separated by settling out and the supernatant is evaporated off under vacuum. 1.1 mg of the title product are isolated in the form of a light oil.

Preparations 7-I and 7-II

2-Chloro-1-(2-phenyl-2,4,6,7-tetrahydropyrazolo[4,3-c]pyridin-5-yl)ethanone (7-I) and 2-chloro-1-(1-phenyl-1,4,6,7-tetrahydropyrazolo[4,3-c]pyridin-5-yl)ethanone (7-II)

Step a) (3-[1-Dimethylaminometh-(Z)-ylidene]-4-oxopiperidine-1-carboxylic) acid tert-butyl ester 10 g of 1-Boc-4-piperidone and 7.2 g of N,N-dimethylformamide dimethylacetate are refluxed in a round-bottomed flask. The crude product thus obtained is column-purified by flash chromatography, and 2.4 g of an oily material are isolated.

Step b) 2-Phenyl-2,4,6,7-tetrahydropyrazolo[4,3-c]pyridine-5-carboxylic acid tert-butyl ester (b-I) and 1-phenyl-1,4,6,7-tetrahydropyrazolo[4,3-c]pyridine-5-carboxylic acid tert-butyl ester (b-II))

The product of step a) (2.4 g) is dissolved in 27 ml of methanol. 1.24 g of phenylhydrazine are added and the mixture is refluxed for 3 hours. Evaporation is carried out under vacuum and column-purification is carried out by flash chromatography using a Biotage® column, elution being carried out with a mixture of ethyl acetate and cyclohexane. 1.8 g of an oily material are isolated.

Step c) (2-Phenyl-2,4,6,7-tetrahydropyrazolo[4,3-c]pyridine-hydrochloride (c-I) and 1-phenyl-1,4,6,7-tetrahydropyrazolo[4,3-c]pyridine-5-hydrochloride (c-II))

The mixture of the products of step b) (b-I and b-II, 2.4 g) is slowly dissolved in 60 ml of trifluoroacetic acid at 0° C. The mixture is then left to stir for 2 hours at ambient temperature. The trifluoroacetic acid is evaporated off, 37% hydrochloric acid is added and the resulting mixture is evaporated to dryness under vacuum. Crystallization is carried out with isopropanol. 1 g of beige solid is obtained.

Step d) 2-Chloro-1-(2-phenyl-2,4,6,7-tetrahydropyrazolo[4,3-c]pyridin-5-yl)ethanone (7-I) and 2-chloro-1-(1-phenyl-1,4,6,7-tetrahydropyrazolo[4,3-c]pyridin-5-yl)ethanone (7-II)

The mixture of the products of step c) (c-I and c-II, 1 g) is suspended in 26 ml of dichloromethane, in a round-bottomed flask with a magnetic stirrer. 1.23 ml of triethylamine are added and the mixture is brought to 0° C. At 0° C., 0.5 ml of chloroacetyl chloride, i.e. the compound of general formula (V) in which Hal=Hal'=Cl and n=1, is run in dropwise. The mixture is left to react for 1 and a half hours and is poured into water. Extraction is carried out with dichloromethane. The organic phase is dried over $Na_2SO_4$, filtered and evaporated under vacuum. The residue is purified by flash chromatography on a Biotage® column, elution being carried out with 9 cyclohexane/1 ethyl acetate. 0.15 g of the title product 7-I (more polar product) is isolated in the form of a light oil and 0.15 g of the title product 7-II (less polar product) is isolated in the form of a light oil.

Preparation 8

2-Chloro-1-[1-(2,2,2-trifluoroethyl)-1,4,6,7-tetrahydropyrazolo[4,3-c]pyridin-5-yl]ethanone By carrying out the procedure as described in preparation 7, but using (2,2,2-trifluoroethyl)hydrazine instead of phenylhydrazine, the title compound is obtained in the form of a light oil.

Preparation 9

2-Chloro-1-(2-pyridin-2-yl-2,4,6,7-tetrahydropyrazolo[4,3-c]pyridin-5-yl)ethanone Step a) 4-(Pyridin-2-ylhydrazono)piperidine-1-carboxylic acid tert-butyl ester The following are charged to a round-bottomed flask with a magnetic stirrer: 5 g of N-Boc-piperidone, 2.45 g of pyridin- 2-ylhydrazine, 100 ml of methanol and 95 ml of a solution of methanol saturated with HCl. The mixture is left to react under a nitrogen stream for 2 h at reflux temperature. The solvent is evaporated off under vacuum, the resulting product is dissolved with dichloromethane and washing is carried out with a saturated aqueous solution of NaHCO$_3$. The organic phase is dried over Na$_2$SO$_4$ and the solvent is evaporated off, and 4.0 g of the title product are isolated in the form of a red oil.

Step b) 2-Pyridin-2-yl-2,4,6,7-tetrahydropyrazolo[4,3-c]pyridine-5-carboxylic acid tert-butyl ester 33 ml of DMF are charged to a round-bottomed flask and 3.7 ml of POCl$_3$ are added slowly at 0° C. The mixture is left to stir at 0° C. for 30 min and then 33 ml of pyridine, 4.0 g of the product of step a) and 5 ml of DMF are added. The mixture is then left to stir for 4 hours at a temperature of 80° C. 270 ml of water are added and extraction is carried out with ethyl acetate. The organic phase is dried over Na$_2$SO$_4$ and the solvent is evaporated off. 4.0 g of the title product are isolated in the form of a black oil, which is purified by flash chromatography on a Biotage® column, elution being carried out with 8 hexane/2 ethyl acetate. 0.78 g of the product is isolated in the form of a yellow solid.

Step c) 2-Pyridin-2-yl-4,5,6,7-tetrahydro-2H-pyrazolo[4,3-c]pyridine hydrochloride 0.78 g of the product of step b) is dissolved at 0° C., in a round-bottomed flask, with 21 ml of trifluoroacetic acid. The solution is then left to stir for 2 hours at ambient temperature.

The trifluoroacetic acid is evaporated off under vacuum, 37% hydrochloric acid is added, and the resulting product is evaporated to dryness under vacuum. Crystallization is carried out with isopropanol. 0.6 g of a beige solid is obtained.

Step d) 2-Chloro-1-[1-(2,2,2-trifluoroethyl)-1,4,6,7-tetrahydropyrazolo[4,3-c]pyridin-5-yl]ethanone 0.3 g of the product of step c) is suspended in 4 ml of dichloromethane, in a round-bottomed flask equipped with a magnetic stirrer. 0.36 ml of triethylamine is added and the mixture is brought to 0° C. At 0° C., 0.12 ml of chloroacetyl chloride, i.e. the compound of general formula (V) in which Hal=Hal'=Cl and n=1, is run in dropwise. The mixture is left to react for 1 and a half hours and poured into water. Extraction is carried out with dichloromethane. The organic phase is dried over Na$_2$SO$_4$, filtered and evaporated under vacuum. The residue is purified by flash chromatography on a Biotage® column, elution being carried out with 9 cyclohexane/1 ethyl acetate. 0.19 g of the title product is isolated in the form of a light oil.

Preparation 10

2-(2,2,2-Trifluoroethyl)-4,5,6,7-tetrahydro-2H-pyrazolo[4,3-c]pyridine hydrochloride By carrying out the procedure as described in Example 9 up to step c) but using (2,2,2-trifluoroethyl)hydrazine instead of pyrid-2-ylhydrazine, the title compound is obtained in the form of a pale yellow solid.

Preparation 11

6-((3R,5S)-4-Carboxymethyl-3,5-dimethylpiperazin-1-yl)nicotinic acid ethyl ester

Step a) 6-((3R,5S)-3,5-Dimethylpiperazin-1-yl)nicotinic acid ethyl ester

By carrying out the procedure as described in preparation 3, but using nicotinic acid ethyl ester instead of 2-trifluoromethyl-6-bromopyridine, the title compound is obtained in the form of a light oil.

Step b) 6-((3R,5S)-4-Benzyloxycarbonylmethyl-3,5-dimethylpiperazin-1-yl)nicotinic acid ethyl ester The following are charged to a round-bottomed flask equipped with a magnetic stirrer: 3.6 g of the product of the preceding step, 132 ml of THF, 2.6 ml of benzylbromoacetate and 4.4 ml of triethylamine. The mixture is left to react under a nitrogen stream overnight at ambient temperature. The solvent is evaporated off and purification is carried out by flash chromatography on a Biotage® column, elution being carried out with 7 hexane/3 ethyl acetate. 2.9 g of the title product are isolated in the form of a clear oil.

Step c) 6-((3R,5S)-4-Carboxymethyl-3,5-dimethylpiperazin-1-yl)nicotinic acid ethyl ester 2.9 g of the product of the preceding step are solubilized in 290 ml of ethanol, and then 1.74 g of Pd/C at 10% are added. The mixture is left to react under a hydrogen stream for 4 hours at a temperature of 40° C. The resulting product is filtered and evaporation is carried out under vacuum, and 2.2 g of the title compound are obtained in the form of a white solid.

Preparation 12

[(2R,6S)-2,6-Dimethyl-4-(5-trifluoromethylpyridin-2-yl)piperazin-1-yl]acetic acid

Step a) [(2R,6S)-2,6-Dimethyl-4-(5-trifluoromethylpyridin-2-yl)piperazin-1-yl]acetic acid ethyl ester By carrying out the procedure as described in step b) of preparation 11, but using the compound of preparation 1 instead of the compound of step a) of preparation 11 and bromoacetic acid ethyl ester instead of bromoacetic acid benzyl ester, the title compound is obtained in the form of solid.

Step b) [(2R,6S)-2,6-Dimethyl-4-(5-trifluoromethylpyridin-2-yl)piperazin-1-yl]acetic acid 2.5 g of the product of the preceding step are solubilized in 22 ml of ethanol, and then 5 ml of a 40% aqueous NaOH solution are added. The mixture is left to react for 3 hours at a temperature of 70° C. The pH is regulated at 6 using a 1N solution of HCl. Extraction is carried out with ethyl acetate. The organic phase is dried over Na$_2$SO$_4$, filtered and evaporated under vacuum. 1.6 g of the title product are isolated in the form of a white solid.

Preparation 13

6-((3R,5S)-3,5-Dimethylpiperazin-1-yl)nicotinic acid methyl ester

By carrying out the procedure as described in preparation 1, but using 6-chloronicotinic acid methyl ester instead of 2-chloro-5-(trifluoromethyl)pyridine, the title compound is obtained in the form of an oil.

Preparation 14

2-Chloro-1-[2-(5-trifluoromethylpyridin-2-yl)-2,4,6,7-tetrahydropyrazolo[4,3-c]pyridin-5-yl]ethanone 1 g of 2-(5-trifluoromethylpyridin-2-yl)-4,5,6,7-tetrahydro-2H-pyrazolo[4,3-c]pyridine hydrochloride is suspended in 12 ml of dichloromethane, in a round-bottomed flask equipped with a magnetic stirrer. 0.95 ml of triethylamine is added and the mixture is brought to 0° C. At 0° C., 0.33 ml of chloroacetyl chloride, i.e. the compound of general formula (V) in which Hal=Hal'=Cl and n=1, is run in dropwise. The mixture is left to react for 1 and a half hours and is poured into water. Extraction is carried out with dichloromethane. The organic phase is dried over $Na_2SO_4$, filtered and evaporated under vacuum. The residue is purified by flash chromatography on a Biotage® column, elution being carried out with 9 cyclohexane/1 ethyl acetate. 1.08 g of the title compound are obtained in the form of a yellow solid.

Preparation 15

8-Pyridin-3-yl-3,8-diazabicyclo[3.2.1]octane hydrochloride

Step a) 3-Benzyl-8-pyridin-3-yl-3,8-diazabicyclo[3.2.1]octane

By carrying out the procedure as described in preparation 3, but using 3-bromopyridine instead of 2-trifluoromethyl-5-bromopyridine and 1-benzyl-3,8-diazabicyclo[3.2.1]octane instead of cis-2,6-dimethylpiperazine, the title compound is obtained in the form of an oil.

Step b) 8-Pyridin-3-yl-3,8-diazabicyclo[3.2.1]octane

The isolated product of 1.1 g is solubilized in 70 ml of ethanol, and then 4 ml of a solution of isopropanol saturated with HCl and 0.6 g of Pd/C at 10% are added. The mixture is left to react under a hydrogen stream for 4 hours at a temperature of 40° C. The resulting product is filtered and evaporation is carried out under vacuum, and 0.84 g of the title compound is obtained.

Preparation 16

(3R,5S)-3,5-Dimethyl-1-(5-(5-methyl-[1,2,4]oxadiazol-3-yl)pyridin-2-yl)piperazine

Step a) 6-((3R,5S)-3,5-Dimethylpiperazin-1-yl)nicotinonitrile

By carrying out the procedure as described in preparation 1, but using 2-chloro-5-cyanopyridine instead of 2-chloro-5-(trifluoromethyl)pyridine, the title compound is obtained in the form of an oil.

Step b) (3R,5S)-3,5-Dimethyl-1-(5-(5-methyl-[1,2,4]oxadiazol-3-yl)pyridin-2-yl)piperazine The following are charged to a round-bottomed flask equipped with a magnetic stirrer: 1 g of the product of the preceding step, 15 ml of ethanol, an aqueous solution of hydroxylamine hydrochloride (2 equivalents), and a solution of 0.98 g of $Na_2SO_4$ in 7.2 ml of water. The mixture is left to react under a nitrogen stream for 4 h at a temperature of 90° C. The precipitate which forms is filtered off and 0.5 g of the resulting crude product (1.7 g) is evaporated under vacuum. It is charged to a round-bottomed flask, to which 20 ml of acetic anhydride are added at 0° C.

The mixture is left to react under a nitrogen stream for 2.5 hours at the reflux temperature. The resulting product is evaporated under vacuum and the residue is taken up with ethyl acetate and a saturated aqueous solution of $K_2CO_3$. The organic phase is dried over $Na_2SO_4$, filtered and evaporated under vacuum.

0.27 g of the resulting crude product is dissolved in 8 ml of 6N HCl. The solution is left to react under a nitrogen stream for 2 h at the reflux temperature. The pH is regulated at 9 with sodium hydroxide and extraction is carried out with ethyl acetate. The organic phase is dried over $Na_2SO_4$, filtered and evaporated under vacuum. The residue is purified by flash chromatography on a Biotage® column, elution being carried out with 8 ethyl acetate/2 methanol. 0.1 g of the title product is obtained in the form of an oil which has a tendency to solidify.

Preparation 17

1-[5-(2H-Pyrazol-3-yl)pyridin-2-yl]piperazine

Step a) 4-(5-Iodopyridin-2-yl)piperazine-1-carboxylic acid tert-butyl ester By carrying out the procedure as described in preparation 1, but using 2-fluoro-5-iodopyridine instead of 2-chloro-5-(trifluoromethyl)pyridine and N-Boc-piperazine instead of cis-2,6-dimethylpiperazine, the title compound is obtained in the form of an oil.

Step b) 4-[5-(2H-Pyrazol-3-yl)pyridin-2-yl]piperazine-1-carboxylic acid tert-butyl ester 0.2 g of compound of step a), 0.069 g of 1H-pyrazole-5-boronic acid, 0.03 g of palladium tetrakis(triphenylphosphine), 0.087 g of sodium bicarbonate, 15 ml of DME and 2 ml of water are charged. The mixture is refluxed for 7 hours. The resulting product is filtered through celite and the solvent is evaporated off. 0.23 g of crude product is isolated. The residue is purified by flash chromatography on a Biotage® column, elution being carried out with 7 hexane/3 ethyl acetate. 0.11 g of the title compound is isolated in the form of a pale yellow solid.

Step c) 1-[5-(2H-Pyrazol-3-yl)pyridin-2-yl]piperazine trifluoroacetate

The compound of step b) (0.11 g) is dissolved slowly in 3.5 ml of trifluoroacetic acid at 0° C. The resulting product is then left to stir for 2 hours at ambient temperature. The trifluoroacetic acid is evaporated off under vacuum and 0.065 g of the title compound is obtained in the form of a white solid.

Preparation 18

(3S,5R)-3,5-Dimethyl-1-(5-thiazol-2-ylpyridin-2-yl) piperazine

Step a) (3S,5R)-3,5-Dimethyl-1-(5-iodopyridin-2-yl) piperazine

By carrying out the procedure as described in preparation 1, but using 2-fluoro-5-iodopyridine instead of 2-chloro-5-(trifluoromethyl)pyridine, the title compound is obtained in the form of an oil.

Step b) (2S,6R)-2,6-Dimethyl-4-(5-iodopyridin-2-yl) piperazine-1-carboxylic acid tert-butyl ester The following are charged under a nitrogen stream at 0° C.: 0.35 g of compound of step a), 0.26 g of (Boc)$_2$O, 0.46 ml of triethylamine and 5 ml of DMF. The mixture is heated at 140° C. for 4 hours. The solvent is evaporated off. 0.49 g of crude product is isolated. The residue is purified by flash chromatography on a Biotage® column, elution being carried out with ethyl acetate. 0.43 g of the title compound is isolated in the form of a pale yellow oil.

Step c) (2S,6R)-2,6-Dimethyl-4-[5-(4,4,5,5-tetramethyl[1,3,2]dioxaborolan-2-yl)pyridin-2-yl]piperazine-1-carboxylic acid tert-butyl ester 0.43 g of compound of step b), 0.29 g of bis(pinacol) diboron, 0.026 g of palladium Cl$_2$ (dppf)$_2$.CH$_2$Cl$_2$, 0.31 g of potassium acetate and 10 ml of DMSO are charged to a round-bottomed flask under a nitrogen stream. The mixture is heated at 85° C. for 2 hours. It is poured into a saturated aqueous solution of NaCl and the mixture is extracted with ethyl acetate. The organic phase is dried over Na$_2$SO$_4$, filtered and evaporated under vacuum. 0.32 g of an oily material is isolated, and is purified by flash chromatography on a Biotage® column, elution being carried out with 9 cyclohexane/1 ethyl acetate. 0.28 g of a yellowish solid is isolated.

Step d) (2S,6R)-2,6-Dimethyl-4-(thiazol-2-ylpyridin-2-yl)piperazine-1-carboxylic acid tert-butyl ester 0.28 g of compound of step c), 0.092 g of 2-bromothiazole, 0.032 g of palladium tetrakistriphenylphosphine (PdP(Ph$_3$)$_4$), 0.094 g of sodium bicarbonate, 20 ml of DME and 3 ml of water are charged to a round-bottomed flask under a nitrogen stream. The mixture is refluxed for 7 hours. It is poured into a saturated aqueous solution of NaCl and extraction is carried out with ethyl acetate. The organic phase is dried over Na$_2$SO$_4$, filtered and evaporated under vacuum. 0.36 g of an oily material is isolated, and is purified by flash chromatography on a Biotage® column, elution being carried out with 9 cyclohexane 9/1 ethyl acetate. 0.2 g of a yellowish oil is isolated.

Step e) (3S,5R)-3,5-Dimethyl-1-(5-thiazol-2-ylpyridin-2-yl)piperazine trifluoroacetate The compound of step d) (0.2 g) is slowly dissolved in 5 ml of trifluoroacetic acid at 0° C. The resulting product is then left to stir for 2 hours at ambient temperature. The trifluoroacetic acid is evaporated off under vacuum and 0.15 g of the title compound is obtained in the form of a beige solid.

EXAMPLE 1

Compound No. 9

2-[(2S,6R)-2,6-Dimethyl-4-(5-trifluoromethylpyridin-2-yl)piperazin-1-yl]-1-(2-phenyl-6,7-dihydro-4H-thiazolo[5,4-c]pyridin-5-yl)ethanone 0.25 g of the compound obtained in preparation 6 (compound of formula (II)), 0.22 g of the compound obtained in preparation 1 (compound of formula (III)), 0.13 g of potassium carbonate and 0.06 g of NaI are reacted in 4 ml of DMF. The reaction is carried out by means of a CEM discover microwave initiator for 30 min at 160° C. The resulting product is poured into water and extraction is carried out with ethyl acetate. The organic phase is dried over Na$_2$SO$_4$, filtered and evaporated under vacuum. 500 mg of an oily material are isolated. Column-purification is carried out by flash chromatography using a Biotage® column, elution being carried out with an 8 cyclohexane/2 ethyl acetate mixture. 400 mg of a pale yellow solid are isolated, and crystallized with ethyl ether. Filtration is carried out and 0.25 g of the title product is obtained in the form of a white solid.

Mp: (169-170)° C.

NMR (apparatus b): δ (ppm, dmso-d6): 1.04 (m, 6H); 2.65-2.76 (m, 2H); 2.82+2.94 (2×m, 2H); 3.15 (m, 2H), 3.64-3.91 (m, 4H); 4.11-4.25 (m, 2H); 4.73+4.89 (2×s, 2H); 6.94 (d, 1H, J=9 Hz); 7.44-7.54 (m, 3H); 7.76 (dd, 1H, J=9 and 2 Hz); 7.89 (m, 2H); 8.38 (bs, 1H).

EXAMPLE 2

Compound No. 18

2-[(2S,6R)-2,6-Dimethyl-4-(6-trifluoromethylpyridin-2-yl)piperazin-1-yl]-1-(2-phenyl-6,7-dihydro-4H-thiazolo[5,4-c]pyridin-5-yl)ethanone By carrying out the procedure as described in Example 1, but using the compound of preparation 3 instead of the compound of preparation 1, the title compound is obtained in the form of a white solid.

Mp: (168-169)° C.

NMR: (apparatus a). δ (ppm, dmso-d6): 1.06 (m, 6H); 2.57-2.65 (m, 2H); 2.76-3.05 (m, 2H); 3.25 (m, *); 3.65-3.92 (m, 6H); 4.75+4.90 (2×bs, 2H); 7.40 (dd, J=8.9 and 2.4 Hz, 1H); 7.45-7.53 (m, 3H); 7.60 (d, J=8.8 Hz, 1H); 7.86-7.92 (m, 2H); 8.39 (d, J=2.7 Hz, 1H).

EXAMPLE 3

Compound No. 19

6-{3-[2-oxo-2-(2-phenyl-2,4,6,7-tetrahydropyrazolo[4,3-c]pyridin-5-yl)ethyl]-3,8-diazabicyclo[3.2.1]oct-8-yl}nicotinic acid methyl ester 0.45 g of the compound obtained in preparation 7-I (compound of formula (II)), 0.45 g of the compound obtained in preparation 4 (compound of formula (III)), 0.6 ml of diisopropylethylamine and 44 ml of DMF are reacted together. The mixture is heated at 100° C. for 2 hours. The resulting product is poured into water and extraction is carried out with ethyl acetate. The organic phase is dried over Na$_2$SO$_4$, filtered and evaporated under vacuum. 700 g of a solid material are isolated. Column-purification is carried out by flash chromatography using a column which is eluted with a 7 hexane/3 ethyl acetate mixture. 0.5 g of the title product is isolated. It is treated with diethyl ether, filtration is carried out, and 0.45 g of a white solid is obtained.

Mp: (204-205)° C.

NMR: (apparatus b). δ (ppm, dmso-d6): 1.73 (m, 2H); 1.81-2.03 (m, 2H); 2.29-2.43 (m, 2H); 2.58-2.65 (m, 1H); 2.66-2.76 (m, 2H); 2.89 (m, 1H); 3.17 (s, 1H); 3.22 (s, *); 3.94 (m, 4H); 3.86 (m, 1H); 4.53-4.70 (m, 3H); 4.77 (bs, 1H); 6.77 (m, 1H); 7.27 (m, 1H); 7.44-7.52 (m, 2H); 7.73-7.79 (m, 2H); 7.92 (m, 1H); 8.28+8.33 (2×s, 1H); 8.63 (m, 1H).

EXAMPLE 4

Compound No. 26

2-[8-(5-Fluoropyrimidin-2-yl)-3,8-diazabicyclo[3.2.1]oct-3-yl]-1-(1-phenyl-1,4,6,7-tetrahydropyrazolo[4,3-c]pyridin-5-yl)ethanone By carrying out the procedure as described in Example 3, but using the compound of preparation 7-II instead of the compound of preparation 7-I and the compound of preparation 2 instead of the compound of preparation 4, the title compound is obtained in the form of a white solid.

Mp: (148-150)° C.

NMR: (apparatus b). δ (ppm, dmso-d6): 1.74 (m, 2H); 1.79-1.99 (m, 2H); 2.31-2.45 (m, 2H); 2.61-2.75 (m, 2H); 2.84 (m, 1H); 2.98 (m, 1H); 3.18+3.22 (2×s, 2H); 3.74+3.83 (2×m, 2H); 4.47-4.65 (m, 3H); 4.71 (s, 1H); 7.33-7.42 (m, 1H), 7.45-7.66 (m, 5H); 8.44 (m, 1H).

EXAMPLE 5

Compound No. 24

6-{3-[2-Oxo-2-(2-phenyl-2,4,6,7-tetrahydropyrazolo[4,3-c]pyridin-5-yl)ethyl]-3,8-diazabicyclo[3.2.1]oct-8-yl}nicotinic acid 0.4 g of the compound of Example 3 is dissolved in 8 ml of 20% aqueous NaOH solution and 8 ml of methanol. The mixture is refluxed for 3 hours. The methanol is evaporated off and the resulting product is washed with ethyl ether. The pH is adjusted to 6 with a 1N HCl solution and extraction is carried out with ethyl acetate. Drying is carried out and the organic phase is evaporated, and 200 mg of an oily material are obtained. The latter is treated with diethyl ether, filtration is carried out, and 0.45 g of a white solid corresponding to the title product is obtained.

Mp: (202-206)° C.

NMR: (apparatus a). δ (ppm, dmso-d6): 1.73 (m, 2H); 1.83-2.01 (m, 2H); 2.28-2.44 (m, 2H); 2.57-2.64 (m, 1H); 2.66-2.77 (m, 2H); 2.89 (m, 1H); 3.16 (s, *); 3.79+3.87 (2×m, 2H); 4.53-4.69 (m, 3H); 4.77 (s, 1H); 6.74 (m, 1H); 7.27 (m, 1H); 7.44-7.51 (m, 2H); 7.73-7.79 (m, 2H); 7.90 (m, 1H); 8.28+8.32 (2×s, 1H); 8.62 (m, 1H); 11.92-12.54 (bs, 1H).

EXAMPLE 6

Compound No. 25

6-{2-oxo-4-[2-oxo-2-(2-phenyl-6,7-dihydro-4H-thiazolo[5,4-c]pyridin-5-yl)ethyl]piperazin-1-yl}nicotinic acid methyl ester By carrying out the procedure as described in Example 3, but using the compound of preparation 6 instead of the compound of preparation 7-I and the compound of preparation 5 instead of the compound of preparation 4, the title compound is obtained in the form of a white solid.

EXAMPLE 7

Compound No. 23

6-{(3S,5R)-3,5-Dimethyl-4-[2-oxo-2-(2-phenyl-2,4,6,7-tetrahydropyrazolo[4,3-c]pyridin-5-yl)ethyl]piperazin-1-yl}nicotinic acid methyl ester hydrochloride By carrying out the procedure as described in Example 1, but using the compound of preparation 7-I instead of the compound of preparation 6 and the compound of preparation 13 instead of the compound of preparation 1, the title compound (free base) is obtained. It is dissolved in isopropanol and then a solution of hydrochloric acid in isopropanol is added. The title product is obtained in the form of a white solid.

Mp: 210-212

NMR (apparatus a, temp. A). δ (ppm, dmso-d6): 1.25+1.32 (2Xm, 6H), 2.75-3.00 (m, 2H), 3.10-3.63 (m, *), 3.66-4.01 (m, 6H), 4.32-4.81 (m, 6H), 7.07 (m, 1H), 7.29 (m, 1H), 7.49 (m, 2H), 7.78 (m, 2H), 8.06 (m, 1H), 8.27-8.40 (m, 1H), 8.71 (m, 1H), 9.19 (bs, 0.5H), 9.44 (bs, 0.5H).

EXAMPLE 8

Compound No. 21

6-{(3S,5R)-3,5-Dimethyl-4-[2-oxo-2-(2-phenyl-2,4,6,7-tetrahydropyrazolo[4,3-c]pyridin-5-yl)ethyl]piperazin-1-yl}nicotinic acid hydrochloride By carrying out the procedure as described in Example 5, but using the compound of Example 7 instead of the compound of Example 3, the title compound (free base) is obtained. It is dissolved in isopropanol and then a solution of hydrochloric acid in isopropanol is added. The title product is obtained in the form of a white solid.

Mp: 209-211

NMR: (temp. B). δ (ppm, dmso-d6): 1.24 (d, J=6.5 Hz, 2.7H), 1.32 (d, J=6.5 Hz, 3.3H), 2.80 (m, 0.8H), 2.94 (m, 1.2H), 3.14-3.30 (m, 1H), 3.44 (m, 1H), 3.49-4.26 (m, *), 4.35-4.80 (m, 6H), 7.01-7.11 (m, 1H), 7.29 (m, 1H), 7.49 (m, 2H), 7.73-7.84 (m, 2H), 8.05 (m, 1H), 8.33 (m, 0.8H), 8.39 (m, 0.2H), 8.66-8.72 (m, 1H), 9.28+9.44 (2 Xbs, 1H), 12.1-13.4 (bs, 1H).

EXAMPLE 9

Compound No. 106

2-(8-Pyridin-3-yl-3,8-diazabicyclo[3.2.1]oct-3-yl)-1-[2-(5-trifluoromethylpyridin-2-yl)-2,4,6,7-tetrahydropyrazolo[4,3-c]pyridin-5-yl]ethanone By carrying out the procedure as described in Example 3, but using the compound of preparation 14 instead of the compound of preparation 7-I and the compound of preparation 15 instead of the compound of preparation 4, the title compound is obtained in the form of a white solid.

Mp: (150-151)° C.

NMR: (temp. B). δ (ppm, dmso-d6): 1.69 (m, 2H), 1.83-1.97 (m, 2H), 2.34-2.66 (m, **), 2.75 (m, 1H), 2.93 (m, 1H), 3.11 (s, 1H), 3.17 (s, 1H), 3.80 (m, 1H), 3.88 (m, 1H), 4.26 (m, 1H), 4.33 (m, 1H), 4.59 (s, 1H), 4.81 (s, 1H), 7.11-7.23 (m, 2H), 7.86 (m, 1H), 8.04 (m, 1H), 8.18 (m, 1H), 8.34 (m, 1H), 8.53 (s, 0.5H), 8.57 (s, 0.5H), 8.86 (m, 1H).

EXAMPLE 10

Compound No. 89

2-{(2S,6R)-2,6-Dimethyl-4-[5-(5-methyl-[1,2,4] oxadiazol-3-yl)pyridin-2-yl]piperazin-1-yl}-1-(2-phenyl-2,4,6,7-tetrahydropyrazolo[4,3-c]pyridin-5-yl)ethanone By carrying out the procedure as described in Example 1, but using the compound of preparation 16 instead of the compound of preparation 1 and the compound of preparation 7-I instead of the compound of preparation 6, the title compound is obtained in the form of a white solid.

Mp: (163-164)° C.

NMR: (temp. B). δ (ppm, dmso-d6): 1.05 (m, 6H), 2.63 (s, 3H), 2.65-2.75 (m, 2.7H), 2.84 (m, 1.3H), 3.17 (m, 2H), 3.67-3.84 (m, 4H), 4.20 (m, 2H), 4.56+4.68 (2Xs, 2H), 6.96 (d, J=9.0 Hz, 1H), 7.27 (m, 1H), 7.47 (m, 2H), 7.76 (m, 2H), 7.99 (dd, J=9.0 and 2.3 Hz, 1H), 8.29 (s, 1H), 8.67 (d, J=2.3 Hz, 1H).

EXAMPLE 11

Compound No. 45

2-[8-(5-Fluoropyrimidin-2-yl)-3,8-diazabicyclo [3.2.1]oct-3-yl]-1-[1-(2,2,2-trifluoroethyl)-1,4,6,7-tetrahydropyrazolo[4,3-c]pyridin-5-yl]ethanone oxalate By carrying out the procedure as described in Example 3, but using the compound of preparation 8 instead of the compound of preparation 7-I and the compound of preparation 2 instead of the compound of preparation 4, the title compound (free base) is obtained. It is dissolved in acetone and then a solution of oxalic acid in acetone is added.

The title product is obtained in the form of a white solid.

Mp: (160-162)° C.

NMR: (temp. A). δ (ppm, dmso-d6): 1.61-1.78 (m, 2H), 1.81-1.98 (m, 2H), 2.34-2.49 (m, 2H), 2.59-2.90 (m, 4H), 3.23+3.32 (2Xs, 2H), 3.78 (m, 2H), 4.40-4.67 (m, 4H), 5.02 (m, 2H), 7.44+7.46 (2Xs, 1H), 8.44 (m, 2H).

EXAMPLE 12

Compound No. 130

6-{(3S,5R)-3,5-Dimethyl-4-[2-oxo-2-(2-phenyl-2,4, 6,7-tetrahydropyrazolo[4,3-c]pyridin-5-yl)ethyl] piperazin-1-yl}nicotinic acid ethyl ester 1.88 g of 2-phenyl-4,5,6,7-tetrahydro-2H-pyrazolo[4,3-c] pyridine hydrochloride are suspended in 123 ml of dichloromethane, in a round-bottomed flask equipped with a magnetic stirrer. 2.5 g of the compound of preparation 11, 4.4 ml of triethylamine and 3.5 g of BOP are added. The mixture is reacted for 1 hour at a temperature of 20-25° C. The resulting product is then poured into water and extraction is carried out with dichloromethane. The organic phase is dried over Na$_2$SO$_4$, filtered and evaporated under vacuum. 6.07 g of an oily material are isolated. Said material is column-purified by flash chromatography using an automatic Biotage® column, elution being carried out with ethyl acetate. 1.8 g of a white solid are isolated.

NMR: (apparatus b, temp. B). δ (ppm, dmso-d6): 1.04 (m, 6H), 1.29 (m, 3H), 2.70 (m, 2H), 2.83+2.94 (2Xm, 2H), 3.16 (m, 2H), 3.63-3.85 (m, 4H), 4.13-4.33 (m, 4H), 4.48-4.77 (m, 2H), 6.87 (m, 1H), 7.27 (m, 1H), 7.47 (m, 2H), 7.76 (m, 2H), 7.92 (m, 1H), 8.29 (bs, 1H), 8.63 (bs, 1H).

EXAMPLE 13

Compound No. 126

2-[(2S,6R)-2,6-Dimethyl-4-(5-trifluoromethylpyridin-2-yl)piperazin-1-yl]-1-[2-(2,2,2-trifluoroethyl)-2, 4,6,7-tetrahydropyrazolo[4,3-c]pyridin-5-yl]ethanone oxalate By carrying out the procedure as described in Example 12, but using the compound of preparation 12 instead of the compound of preparation 11 and the compound of preparation 10 instead of 2-phenyl-4,5,6,7-tetrahydro-2H-pyrazolo [4,3-c]pyridine hydrochloride, the title compound (free base) is obtained. It is dissolved in acetone and then a solution of oxalic acid in acetone is added. The title product is obtained in the form of a white solid.

NMR: (apparatus b, temp. B). δ (ppm, dmso-d6): 1.11 (m, 6H), 2.57-3.07 (m, 4H), 3.10-4.73 (m, *), 5.04 (m, 2H), 7.02 (m, 1H), 7.65 (m, 1H), 7.82 (m, 1H), 8.42 (m, 1H).

EXAMPLE 14

Compound No. 134

1-(2-Phenyl-6,7-di hydro-4H-thiazolo[5,4-c]pyridin-5-yl)-2-{4-[5-(2H-pyrazol-3-yl)pyridin-2-yl]piperazin-1-yl}ethanone By carrying out the procedure as described in Example 3, but using the compound of preparation 17 instead of the compound of preparation 4 and the compound of preparation 6 instead of the compound of preparation 7-I, the title compound is obtained in the form of a white solid.

Mp: (231-237)° C.

NMR: (apparatus a, temp. B). δ (ppm, dmso-d6): 2.34-2.69 (m, *), 2.85+3.00 (2xm, 2H), 3.16-3.68 (m, **), 3.89 (m, 2H), 4.67-5.05 (m, 2H), 6.62 (m, 1H), 6.89 (m, 1H), 7.49 (m, 3H), 7.74 (m, 1H), 7.83-8.01 (m, 3H), 8.56 (m, 1H), 12.68-13.26 (m, 1H).

EXAMPLE 15

Compound No. 135

2-[(2S,6R)-2,6-Dimethyl-4-(5-thiazol-2-ylpyridin-2-yl)piperazin-1-yl]-1-(2-phenyl-2,4,6,7-tetrahydropyrazolo[4,3-c]pyridin-5-yl)ethanone By carrying out the procedure as described in Example 1, but using the compound of preparation 7-I instead of the compound of preparation 6 and the compound of preparation 18 instead of the compound of preparation 1, the title compound is obtained in the form of a free base.

Mp (173-174)° C.

NMR: (apparatus a, temp. B). δ (ppm, dmso-d6): 1.05 (m, 6H), 2.67 (m, 3H), 2.84 (m, 1H), 3.17 (m, 2H), 3.63-3.87 (m, 4H), 4.18 (m, 2H), 4.50-4.74 (m, 2H), 6.93 (d, J=9.0 Hz, 1H), 7.27 (m, 1H), 7.47 (m, 2H), 7.64 (d, J=3.3 Hz, 1H), 7.76 (m, 2H), 7.83 (d, J=3.3 Hz, 1H), 8.00 (dd, J=9.0 et 2.4 Hz, 1H), 8.29 (s, 1H), 8.66 (d, J=2.4 Hz, 1H).

The following table describes the examples obtained by application and/or adaptation of the methods described, by means of the appropriate reactants and starting products:

| No. | A | W | R2 | n | Salt | Mp | LCMS |
|---|---|---|---|---|---|---|---|
| 1 | thieno-tetrahydropyridine | diazabicyclo | 5-F, 2-Me-pyrimidine | 1 | — | 178-180 | MH+ 388 r.t. 4.3' Method A |
| 2 | 2-phenyl-thiazolo-tetrahydropyridine | diazabicyclo | 5-F, 2-Me-pyrimidine | 1 | — | 180-181 | MH+ 465 r.t. 5.2' Method A |
| 3 | 2-Cl-naphthyridine | diazabicyclo | 5-F, 2-Me-pyrimidine | 1 | — | 210-212 | M+ = 417 r.t. 4.3' Method A |
| 4 | 2-phenyl-pyrazolo-tetrahydropyridine | diazabicyclo | 5-F, 2-Me-pyrimidine | 1 | — | 200-201 | M+ = 448 r.t. 4.7' Method A |
| 5 | 2-phenyl-thiazolo-tetrahydropyridine | diazabicyclo | 6-Me-pyridine-3-COOCH$_3$ | 1 | — | 160-162 | M+ = 504 r.t. 5.1' Method A |
| 6 | 2-phenyl-thiazolo-tetrahydropyridine | dimethyl-piperazine | 6-Me-pyridine-3-COOCH$_3$ | 1 | HCl | 192-195 | M+ = 506 r.t. 5.2' Method A |
| 7 | 2-phenyl-thiazolo-tetrahydropyridine | diazabicyclo | 6-Me-pyridine-3-COOH | 1 | — | 156-157 | M+ = 490 r.t. 4.4' Method A |

-continued (I)

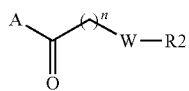

| No. | A | W | R2 | n | Salt | Mp | LCMS |
|---|---|---|---|---|---|---|---|
| 8 | 2-phenyl-thiazolo tetrahydropyridine | (2S,5R)-dimethylpiperazine | 6-methyl-pyridine-3-COOH | 1 | HCl | 222-225 | M+ = 492 r.t. 4.7' Method A |
| 9 | 2-phenyl-thiazolo tetrahydropyridine | (2S,5R)-dimethylpiperazine | 6-methyl-5-CF₃-pyridine | 1 | — | 169-170 | M+ = 516 r.t. 5.5' Method A |
| 10 | 2-phenyl-pyrazolo tetrahydropyridine | (2S,5R)-dimethylpiperazine | 6-methyl-5-CF₃-pyridine | 1 | — | 175-177 | M+ = 489 r.t. 5.1' Method A |
| 11 | 2-phenyl-thiazolo tetrahydropyridine | 2-oxopiperazine | 6-methyl-5-CF₃-pyridine | 1 | — | 165-166 | M+ = 502 r.t. 7.2' Method A |
| 12 | 2-phenyl-thiazolo tetrahydropyridine | piperazine | 6-methyl-5-CF₃-pyridine | 1 | — | 164-165 | M+ = 488 r.t. 5.3' Method A |
| 13 | 2-phenyl-pyrazolo tetrahydropyridine | piperazine | 6-methyl-5-CF₃-pyridine | 1 | — | 133-134 | M+ = 471 r.t. 5.0' Method A |
| 14 | 2-phenyl-pyrazolo tetrahydropyridine | 2-oxopiperazine | 6-methyl-5-CF₃-pyridine | 1 | — | 141-142 | M+ = 485 r.t. 6.6' Method A |

-continued

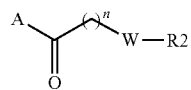
(I)

| No. | A | W | R2 | n | Salt | Mp | LCMS |
|---|---|---|---|---|---|---|---|
| 15 | 2-phenyl-thiazolo-tetrahydropyridine | (2S,6R)-dimethylpiperazine | 5-fluoro-2-methylpyrimidine | 1 | — | 182-184 | M+ = 467 r.t. 4.9' Method A |
| 16 | 2-phenyl-pyrazolo-tetrahydropyridine | (2S,6R)-dimethylpiperazine | 5-methylpyrimidine | 1 | HCl | 166-167 | M+ = 432 r.t. 3.9' Method A |
| 17 | 2-phenyl-pyrazolo-tetrahydropyridine | (2S,6R)-dimethylpiperazine | 5-fluoro-2-methylpyrimidine | 1 | — | 174-175 | M+ = 450 r.t. 4.4' Method A |
| 18 | 2-phenyl-thiazolo-tetrahydropyridine | (2S,6R)-dimethylpiperazine | 2-CF3-5-methylpyridine | 1 | — | 168-169 | M+ = 516 r.t. 5.1' Method A |
| 19 | 2-phenyl-pyrazolo-tetrahydropyridine | diazabicyclooctane | 5-COOCH3-6-methylpyridine | 1 | — | 204-205 | M+ = 487 r.t. 5.3' Method A |
| 20 | 2-phenyl-pyrazolo-tetrahydropyridine | (2S,6R)-dimethylpiperazine | 2-CF3-5-methylpyridine | 1 | — | 174-175 | M+ = 499 r.t. 4.9' Method A |
| 21 | 2-phenyl-pyrazolo-tetrahydropyridine | (2S,6R)-dimethylpiperazine | 5-COOH-6-methylpyridine | 1 | HCl | 209-211 | M+ = 475 r.t. 4.3' Method A |

-continued
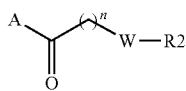
(I)
| No. | A | W | R2 | n | Salt | Mp | LCMS |
|---|---|---|---|---|---|---|---|
| 22 | | | | 1 | — | 215-216 | M+ = 449 r.t. 3.7' Method A |
| 23 | | | | 1 | HCl | 210-212 | M+ = 489 r.t. 4.8' Method A |
| 24 | | | | 1 | — | 202-206 | M+ = 473 r.t. 4.0' Method A |
| 25 | | | | 1 | — | 191-192 | M+ = 492 r.t. 5.6' Method A |
| 26 | | | | 1 | — | 148-150 | M+ = 448 r.t. 4.3' Method A |
| 27 | | | | 1 | — | — | M+ = 417 r.t. 3.0' Method A |
| 28 | | | | 1 | — | 165-168 | M+ = 429 r.t. 3.6' Method A |

-continued
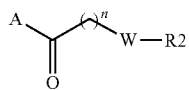
(I)
| No. | A | W | R2 | n | Salt | Mp | LCMS |
|---|---|---|---|---|---|---|---|
| 29 | | | | 1 | — | 212-213 | M+ = 497 r.t. 5.4' Method A |
| 30 | | | | 1 | HCl | 142-145 | M+ = 434 r.t. 3.2' Method A |
| 31 | | | | 1 | — | 197-198 | M+ = 430 r.t. 3.7' Method A |
| 32 | | | | 1 | — | 147-149 | M+ = 386 r.t. 3.3' Method A |
| 33 | | | | 1 | — | 252-253 | M+ = 490 r.t. 4.9' Method A |
| 34 | | | | 1 | — | 191-193 | M+ = 532 r.t. 6.2' Method A |
| 35 | | | | 1 | — | 173-175 | M+ = 532 r.t. 6.3' Method A |
| 36 | | | | 1 | — | 137-138 | M+ = 403 r.t. 3.6' Method A |

-continued

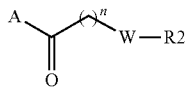
(I)

| No. | A | W | R2 | n | Salt | Mp | LCMS |
|---|---|---|---|---|---|---|---|
| 37 | OMe-phenyl-thiazolo-tetrahydropyridine-N- | diazabicyclo | 6-methyl-pyridine-3-COOCH₃ | 1 | — | 159-160 | M+ = 534 r.t. 5.1' Method A |
| 38 | F-phenyl-thiazolo-tetrahydropyridine-N- | diazabicyclo | 6-methyl-pyridine-3-COOCH₃ | 1 | — | 192-193 | M+ = 523 r.t. 5.3' Method A |
| 39 | CF₃-pyridyl-pyrazolo-tetrahydropyridine-N- | diazabicyclo | 6-methyl-pyridine-3-COOCH₃ | 1 | — | 217-218 | M+ = 556 r.t. 5.4' Method A |
| 40 | CF₃-pyridyl-pyrazolo-tetrahydropyridine-N- | diazabicyclo | 5-F-2-methyl-pyrimidine | 1 | — | 208-209 | M+ = 517 r.t. 5.1' Method A |
| 41 | phenyl-pyrimido-tetrahydropyridine-N- | piperazinone | 2-methyl-5-CF₃-pyridine | 1 | — | — | M+ = 497 r.t. 6.0' Method A |
| 42 | thienyl-thiazolo-tetrahydropyridine-N- | piperazinone | 2-methyl-5-CF₃-pyridine | 1 | — | 179-180 | M+ = 508 r.t. 6.0' Method A |
| 43 | MeO-phenyl-imidazo-tetrahydropyridine-N- | diazabicyclo | 2-methyl-5-F-pyrimidine | 1 | — | 186-188 | M+ = 478 r.t. 1.48' Method A |
| 44 | thienyl-thiazolo-tetrahydropyridine-N- | diazabicyclo | 6-methyl-pyridine-3-COOH | 1 | — | 262-264 | M+ = 496 r.t. 4.19' Method A |

-continued
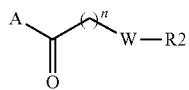
(I)
| No. | A | W | R2 | n | Salt | Mp | LCMS |
|-----|---|---|----|---|------|-----|------|
| 45 | | | | 1 | oxalate | 160-162 | M+ = 454 r.t. 3.81' Method A |
| 46 | | | | 1 | — | 194-195 | M+ = 478 r.t. 4.3' Method A |
| 47 | | | | 1 | — | 122-123 | M+ = 372 r.t. 3.17' Method A |
| 48 | | | | 1 | — | — | M+ = 487 r.t. 4.65' Method A |
| 49 | | | | 1 | — | — | M+ = 473 r.t. 3.95 Method A |
| 50 | | | | 1 | — | 142-143 | M+ = 428 r.t. 4.05' Method A |
| 51 | | | | 1 | — | 151-152 | M+ = 466 r.t. 4.29' Method A |
| 52 | | | | 1 | — | 156-159 | M+ = 456 r.t. 4.61' Method A |

-continued

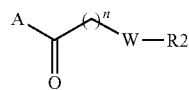
(I)

| No. | A | W | R2 | n | Salt | Mp | LCMS |
|---|---|---|---|---|---|---|---|
| 53 | phenyl-N=CH-(N-methyl-piperidinylidene) | 2,5-dimethylpiperazine | 6-methyl-pyridine-3-COOH | 1 | — | 165-167 | M+ = 475 r.t. 4.05' Method A |
| 54 | 2-phenyl-furo[3,2-c]pyridine (N-methyl) | 2,5-diazabicyclo[2.2.1] | 2-methyl-5-fluoro-pyrimidine | 1 | — | 165-167 | M+ = 448 r.t. 5.54 Method A |
| 55 | 2-phenyl-1H-pyrrolo[3,2-c]pyridine (N-methyl) | 2,5-diazabicyclo[2.2.1] | 2-methyl-5-fluoro-pyrimidine | 1 | — | 240-242 | M+ = 447 r.t. 5.11 Method A |
| 56 | 2-phenyl-thiazolo[5,4-c]pyridine (N-methyl) | 2,5-diazabicyclo[2.2.1] | 6-methyl-pyridine-3-COOMe | 1 | — | 162-163 | M+ = 504 r.t. 4.69' Method A |
| 57 | phenyl-N=CH-(N-methyl-piperidinylidene) | 2,5-diazabicyclo[2.2.1] | 6-methyl-pyridine-3-COOMe | 1 | — | 157-158 | M+ = 487 r.t. 4.39' Method A |
| 58 | 2-phenyl-oxazolo[5,4-c]pyridine (N-methyl) | 2,5-diazabicyclo[2.2.1] | 2-methyl-5-fluoro-pyrimidine | 1 | — | 88-89 | M+ = 449 r.t. 4.67' Method A |
| 59 | 2-phenyl-thiazolo[5,4-c]pyridine (N-methyl) | 2,5-dimethylpiperazine | 6-methyl-pyridine-3-CN | 1 | — | 159-160 | M+ = 473 r.t. 4.8' Method A |

-continued
(I)
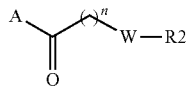
| No. | A | W | R2 | n | Salt | Mp | LCMS |
|---|---|---|---|---|---|---|---|
| 60 | | | | 1 | — | 190-192 | M+ = 528 r.t. 5.1' Method A |
| 61 | | | | 1 | — | 207-208 | M+ = 473 r.t. 3.82' Method A |
| 62 | | | | 1 | — | 250-251 | M+ = 490 r.t. 4.09' Method A |
| 63 | | | | 1 | — | 220-221 | M+ = 490 r.t. 4.27' Method A |
| 64 | | | | 1 | — | 193-194 | M+ = 466 r.t. 3.48 Method A |
| 65 | | | | 1 | — | 200-201 | M+ = 554 r.t. 6.88' Method A |
| 66 | | | | 1 | oxalate | 82-83 | M+ = 491 r.t. 5.31' Method A |
| 67 | | | | 1 | — | 212-213 | M+ = 460 r.t. 4.75' Method A |

-continued

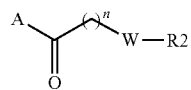
(I)

| No. | A | W | R2 | n | Salt | Mp | LCMS |
|---|---|---|---|---|---|---|---|
| 68 | phenyl-N=C-piperidine-N-Me | bicyclic diamine | 3-(6-methylpyridin-3-yl)-1,2,4-oxadiazol-5(4H)-one | 1 | — | 176-179 | M+ = 513 r.t. 4.38' Method A |
| 69 | 2-phenyl-imidazo-tetrahydropyridine-N-Me | bicyclic diamine | 2-methyl-5-fluoropyrimidine | 1 | — | 130-132 | M+ = 448 r.t. 3.26' Method A |
| 70 | 2-phenyl-thiazolo-tetrahydropyridine-N-Me | bicyclic diamine | 3-(6-methylpyridin-3-yl)-1,2,4-oxadiazol-5(4H)-one | 1 | — | 215-218 | M+ = 530 r.t. 4.65' Method A |
| 71 | 2-phenyl-thiazolo-tetrahydropyridine-N-Me | bicyclic diamine | 2-methyl-5-fluoropyrimidine | 1 | — | 180-184 | M+ = 465 r.t. 5.02' Method A |
| 72 | 2-phenyl-thiazolo-tetrahydropyridine-N-Me | (2R,6S)-2,6-dimethylpiperazine | 2-methylpyrimidine-5-COOH | 1 | sodium salt | 269-272 | M+ = 493 r.t. 4.24' Method A |
| 73 | 2-(pyridin-3-yl)-thiazolo-tetrahydropyridine-N-Me | bicyclic diamine | 2-methyl-5-fluoropyrimidine | 1 | — | 200-202 | M+ = 466 r.t. 3.76' Method A |
| 74 | 2-phenyl-thiazolo-tetrahydropyridine-N-Me | bicyclic diamine | 5-(6-methylpyridin-3-yl)tetrazole | 1 | — | 201-202 | M+ = 514 r.t. 4.4' Method A |

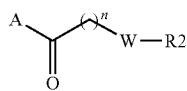
(I)
| No. | A | W | R2 | n | Salt | Mp | LCMS |
|---|---|---|---|---|---|---|---|
| 75 | | | COOH | 1 | — | 94-97 | M+ = 476 r.t. 3.9' Method A |
| 76 | | | CN | 1 | — | 212-213 | M+ = 489 r.t. 5.21' Method A |
| 77 | | | CN | 1 | — | 198-200 | M+ = 454 r.t. 4.53' Method A |
| 78 | | | CF3 | 1 | — | 198-200 | M+ = 485 r.t. 3.94' Method A |
| 79 | | | COOEt | 1 | HCl | 235-236 | M+ = 503 r.t. 4.6' Method A |
| 80 | | | F | 1 | — | 196-198 | M+ = 483 r.t. 4.9' Method A |
| 81 | | | F | 1 | — | 203-207 | M+ = 495 r.t. 4.82' Method A |

-continued
(I)
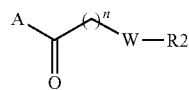
| No. | A | W | R2 | n | Salt | Mp | LCMS |
|---|---|---|---|---|---|---|---|
| 82 | | | | 1 | — | 140-142 | M+ = 502 r.t. 6.26 Method A |
| 83 | | | | 1 | — | 140-142 | M+ = 486 r.t. 6.33' Method A |
| 84 | | | | 1 | — | 180-183 | M+ = 503 r.t. 5.03' Method A |
| 85 | | | | 1 | — | 230-231 | M+ = 511 r.t. 4.42' Method A |
| 86 | | | | 1 | — | 198-199 | M+ = 513 r.t. 4.05 Method A |
| 87 | | | | 1 | — | 182-183 | M+ = 513 r.t. 4.3' Method A |
| 88 | | | | 1 | — | 162-164 | M+ = 516 r.t. 5.08' Method A |

-continued
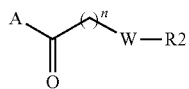
(I)
| No. | A | W | R2 | n | Salt | Mp | LCMS |
|---|---|---|---|---|---|---|---|
| 89 | | | | 1 | — | 163-164 | M+ = 513 r.t. 4.48' Method A |
| 90 | | | | 1 | — | 189-190 | M+ = 499 r.t. 4.03' Method A |
| 91 | | | | 1 | — | 168-171 | M+ = 513 r.t. 4.48 Method A |
| 92 | | | | 1 | — | 134-135 | M+ = 469 r.t. 4.06' Method A |
| 93 | | | | 1 | — | 150-151 | M+ = 455 r.t. 3.61' Method A |
| 94 | | | | 1 | — | — | M+ = 453 r.t. 3.67' Method A |
| 95 | | | | 1 | — | 193 | M+ = 449 r.t. 4.62' Method A |
| 96 | | | | 1 | — | 175 | M+ = 486 r.t. 5.96' Method A |

-continued

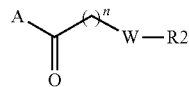

(I)

| No. | A | W | R2 | n | Salt | Mp | LCMS |
|---|---|---|---|---|---|---|---|
| 97 | 2-phenyl-furo[3,2-c]tetrahydropyridine | (2S,5R)-dimethylpiperazine | 5-CF3-2-methylpyridine | 1 | — | 162 | M+ = 499 r.t. 5.66' Method A |
| 98 | 2-phenyl-pyrazolo-tetrahydropyridine | (2S,5R)-dimethylpiperazine | isopropyl 6-methylnicotinate | 1 | — | 135-136 | M+ = 517 r.t. 4.87' Method A |
| 99 | methylaminomethylene-N-methylpiperidone | diazabicyclo | 5-CF3-2-methylpyridine | 1 | — | 70-71 | M+ = 435 r.t. 4.06 Method A |
| 100 | methylaminomethylene-N-methylpiperidone | (2S,5R)-dimethylpiperazine | 5-CF3-2-methylpyridine | 1 | HCl | 50-51 | M+ = 437 r.t. 3.93' Method A |
| 101 | 2-phenyl-furo[3,2-c]tetrahydropyridine | diazabicyclo | 5-CF3-2-methylpyridine | 1 | — | 155 | M+ = 497 r.t. 6.21' Method A |
| 102 | 2-(4-fluorophenyl)-thiazolo-tetrahydropyridine | diazabicyclo | 6-methylnicotinic acid | 1 | — | 240-244 | M+ = 508 r.t. 4.56 Method A |
| 103 | 5-CF3-pyridyl-aminomethylene-N-methylpiperidone | (2S,5R)-dimethylpiperazine | 5-CF3-2-methylpyridine | 1 | — | 190-191 | M+ = 568 r.t. 5.55' Method A |
| 104 | 5-CF3-pyridyl-aminomethylene-N-methylpiperidone | diazabicyclo | 5-CF3-2-methylpyridine | 1 | — | 192-193 | M+ = 566 r.t. 5.91' Method A |

-continued
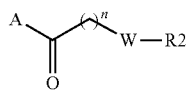
(I)
| No. | A | W | R2 | n | Salt | Mp | LCMS |
|---|---|---|---|---|---|---|---|
| 105 | | | | 1 | — | 120-121 | M+ = 455 r.t. 3.53' Method A |
| 106 | | | | 1 | — | 150-151 | M+ = 498 r.t. 3.99' Method A |
| 107 | | | | 1 | — | 140-141 | M+ = 553 r.t. 4.71' Method A |
| 108 | | | | 1 | — | 185-186 | M+ = 507 r.t. 4.77' Method A |
| 109 | | | | 1 | — | 150-152 | M+ = 497 r.t. 3.91' Method A |
| 110 | | | | 1 | — | 189-192 | M+ = 499 r.t. 3.75' Method A |
| 111 | | | | 1 | — | 150-151 | M+ = 501 r.t. 4.59' Method A |

-continued

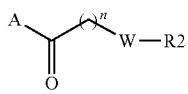
(I)

| No. | A | W | R2 | n | Salt | Mp | LCMS |
|---|---|---|---|---|---|---|---|
| 112 | 5-CF₃-pyridin-2-yl-N=CH-(1-methylpiperidin-3-ylidene) | (2S,6R)-2,6-dimethylpiperazine | 5-chloro-2-methylpyridine | 1 | — | 165-166 | M+ = 534 r.t. 5.39' Method A |
| 113 | 2-phenyl-5-methyl-4,5,6,7-tetrahydro-2H-pyrazolo[4,3-c]pyridine | piperazine | 7-chloro-4-methylquinoline | 1 | — | 100-101 | M+ = 487 r.t. 3.7' Method A |
| 114 | phenyl-N=CH-(1-methylpiperidin-3-ylidene) | piperazine | 6-chloro-2-methylpyridine | 1 | — | 155-156 | M+ = 437 r.t. 4.46' Method A |
| 115 | 2-(pyridin-4-yl)-5-methyl-4,5,6,7-tetrahydrothiazolo[5,4-c]pyridine | 2,5-diazabicyclo[2.2.1]heptane | 5-CF₃-2-methylpyridine | 1 | — | 183-185 | M+ = 515 r.t. 4.35' Method A |
| 116 | 2-phenyl-5-methyl-4,5,6,7-tetrahydro-imidazo[4,5-c]pyridine | (2S,6R)-2,6-dimethylpiperazine | 6-methyl-nicotinic acid | 1 | — | 190-192 | M+ = 475 r.t. 2.86' Method A |
| 117 | pyridin-2-yl-N=CH-(1-methylpiperidin-3-ylidene) | 2,5-diazabicyclo[2.2.1]heptane | 5-CF₃-2-methylpyridine | 1 | — | 170-171 | M+ = 498 r.t. 5' Method A |
| 118 | 2-(pyridin-2-yl)-5-methyl-4,5,6,7-tetrahydro-2H-pyrazolo[4,3-c]pyridine | (2S,6R)-2,6-dimethylpiperazine | 5-CF₃-2-methylpyridine | 1 | — | 165-166 | M+ = 500 r.t. 4.79' Method A |

-continued

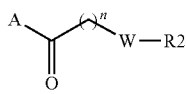

(I)

| No. | A | W | R2 | n | Salt | Mp | LCMS |
|---|---|---|---|---|---|---|---|
| 119 | 2-pyridyl-pyrazolo-tetrahydropyridine | methylpiperazinone | 2-methyl-5-CF3-pyridyl | 1 | — | 139-140 | M+ = 486 r.t. 5.23' Method A |
| 120 | 4-F-phenyl-imidazo-tetrahydropyridine | methylpiperazinone | 2-methyl-5-CF3-pyridyl | 1 | — | 190-192 | M+ = 503 r.t. 4.11' Method A |
| 121 | 2-pyridyl-pyrazolo-tetrahydropyridine | diazabicyclooctane | 3-pyridyl | 1 | — | 61-62 | M+ = 430 r.t. 3.09' Method A |
| 122 | CF3-ethyl-pyrazolo-tetrahydropyridine | diazabicyclooctane | 2-methyl-5-CF3-pyridyl | 1 | — | — | M+ = 503 r.t. 4.68' Method A |
| 123 | 4-F-phenyl-imidazo-tetrahydropyridine | diazabicyclooctane | 2-methyl-5-CF3-pyridyl | 1 | — | 148-150 | M+ = 515 r.t. 4.08' Method A |
| 124 | 4-F-phenyl-imidazo-tetrahydropyridine | dimethylpiperazine | 2-methyl-5-CF3-pyridyl | 1 | — | 145-147 | M+ = 517 r.t. 3.77' Method A |
| 125 | CF3-ethyl-pyrazolo-tetrahydropyridine | methylpiperazinone | 2-methyl-5-CF3-pyridyl | 1 | — | — | M+ = 491 r.t. 4.89' Method A |

-continued
(I)
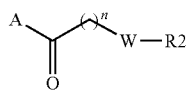
| No. | A | W | R2 | n | Salt | Mp | LCMS |
|---|---|---|---|---|---|---|---|
| 126 | | | | 1 | oxalate | 151-153 | M+ = 505 r.t. 4.54' Method A |
| 127 | | | | 1 | — | 174-175 | M+ = 483 r.t. 4.59' Method A |
| 128 | | | | 1 | — | 176-177 | M+ = 527 r.t. 5.34' Method A |
| 129 | | | | 1 | — | 203-204 | M+ = 481 r.t. 4.17' Method A |
| 130 | | | | 1 | — | — | M+ = 503 r.t. 4.66' Method A |
| 131 | | | | 1 | — | 103-105 | M+ = 509 r.t. 4.07' Method A |
| 132 | | | | 1 | — | 159-161 | M+ = 497 r.t. 4.69' Method A |

-continued (I)

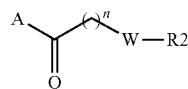

| No. | A | W | R2 | n | Salt | Mp | LCMS |
|---|---|---|---|---|---|---|---|
| 133 | 4-MeO-phenyl-thiazolo[5,4-c]pyridine | diazabicyclic | 2-methyl-5-CF3-pyridine | 1 | — | 70-73 | M+ = 530 r.t. 4.97' Method A |
| 134 | 2-phenyl-thiazolo[5,4-c]pyridine | piperazine | 2-methyl-5-(pyrazolyl)-pyridine | 1 | — | 231-237 | M+ = 486 r.t. 4.13' Method A |
| 135 | phenyl-iminomethyl-piperidine | 2,6-dimethylpiperazine | 2-methyl-5-(thiazolyl)-pyridine | 1 | — | 173-174 | M+ = 514 r.t. 4.56' Method A |
| 136 | 2-phenyl-thiazolo[5,4-c]pyridine | diazabicyclic | 2-methyl-5-(thiazolyl)-pyridine | 1 | — | — | M+ = 529 r.t. 5.04' Method A |
| 137 | phenyl-iminomethyl-piperidine | diazabicyclic | 2-methyl-5-(oxadiazolyl)-pyridine | 1 | — | 201-202 | M+ = 497 r.t. 4.45' Method A |
| 138 | 2-ethyl-pyrazolo[3,4-c]pyridine | diazabicyclic | 2-methyl-5-CF3-pyridine | 1 | — | 99-100 | M+ = 449 r.t. 4.37' Method A |
| 139 | phenyl-iminomethyl-piperidine | 2,6-dimethylpiperazine | 2-methyl-5-(oxadiazolyl)-pyridine | 1 | — | — | M+ = 499 r.t. 4.21' Method A |

-continued
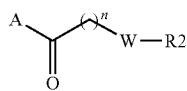
(I)
| No. | A | W | R2 | n | Salt | Mp | LCMS |
|---|---|---|---|---|---|---|---|
| 140 | | | | 1 | — | 147-150 | M+ = 476 r.t. 4.0' Method B |
| 141 | | | | 1 | — | 163-164 | M+ = 432 r.t. 4.56' Method B |
| 142 | | | | 1 | — | 180-181 | M+ = 450 r.t. 3.14' Method A |
| 143 | | | | 1 | — | 196-197 | M+ = 500 r.t. 6.29' Method B |
| 144 | | | | 1 | — | — | M+ = 490 r.t. 4.22' Method A |
| 145 | | | | 1 | — | 207-209 | M+ = 431 r.t. 4.69' Method B |
| 146 | | | | 1 | — | — | M+ = 501 r.t. 4.32' Method A |

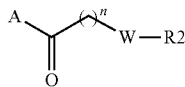

| No. | A | W | R2 | n | Salt | Mp | LCMS |
|---|---|---|---|---|---|---|---|
| 147 | | | CF₃ pyridine | 1 | — | — | M+ = 451<br>r.t. 4.35'<br>Method A |
| 148 | | | CF₃ pyridine | 1 | — | 151-152 | M+ = 437<br>r.t. 4.44'<br>Method A |
| 149 | | | COOH pyridine | 1 | — | 208-209 | M+ = 475<br>r.t. 3.98'<br>Method A |
| 150 | | | COOH pyridine | 1 | 2HCl<br>2H2O | 252-253 | M+ = 475<br>r.t. 3.95'<br>Method A |

The compounds according to the invention were the subject of biochemical studies.

Cell Culture:

The SH-SY-5Y strain (human neuroblastoma) is cultured conventionally in a DMEM culture medium (Dulbecco's Modified Eagle's Medium) (Gibco BRL, France) containing FCS (5%) (foetal calf serum) (Boehringer Mannheim, Germany), sodium pyruvate (1 mM) and glutamine (4 mM) in culture flasks coated with collagen (Becton Dickinson, France).

The SK-N-BE parent strain (human neuroblastoma) and the Bep 75 clone, stably expressing the whole form of the human p75$^{NTR}$ receptor (SK-N-BE Bep 75) are cultured conventionally in an RPMI culture medium containing FCS (5%), sodium pyruvate (1 mM) and glutamine (4 mM). For the SK-N-BE Bep 75 cells, hygromycin (200 µl/20 ml of medium) is added as selection agent.

Study of the dimerization of the p75$^{NTR}$ receptor independently of its ligand.

The p75$^{NTR}$ receptor dimerization study is carried out on a cell suspension of the SK-N-BE Bep 75 strain. The cells (2.5×10⁴ cells/well) are placed in wells (96-well plate) for 24 h, and then preincubated for 1 h at 37° C. in the presence or absence of the compounds according to the invention. Supernatant is then added, this supernatant being derived from the culture of HEK293 human cells of renal origin expressing, after 48 h of transfection, and secreting a soluble form of the p75$^{NTR}$ receptor (extracellular part of the receptor) coupled to an alkaline phosphatase, at the final concentration of 10 nM. The quantification of the specific binding of the soluble p75$^{NTR}$ receptor to the receptor present on SK-N-BE Bep 75 cells is determined by measuring the alkaline phosphatase enzyme activity after incubation of the cells for 1 hour at 37° C. in the presence of the supernatant. After filtration and transfer of the filters into 24-well plates, the alkaline phosphatase activity is determined by adding CDP-Star chemiluminescent substrate (ready-to-use, Roche). The concentrations inhibiting 50% (Cl$_{50}$) of the dimerization of the p75$^{NTR}$ receptor, of the compounds according to the invention, are low and range from 10$^{-6}$ to 10$^{-11}$M.

For example, compounds No. 9, 11, 19 and 24 showed an IC$_{50}$ of 0.73 nM, 1.9 nM, 14 nM and 1.55 nM, respectively.

Measurement of Apoptosis

The cells (human neuroblastoma strains SH-SY-5Y and SK-N-BE Bep 75) are placed in 35 mm diameter Petri dishes (Biocoat collagen I, (10⁵ cells/well)) in an appropriate culture medium containing 5% of FCS, for 24 h. The culture medium is then removed, the cells are rinsed with PBS (Dulbecco's Phosphate buffered saline), and then either fresh medium containing 5% of FCS or medium containing NGF (at the concentration of 10 ng/ml), or beta-amyloid peptide (Aβ1-40) (at the concentration of 10 µM) is added, this being in the presence or absence of the compounds according to the invention. The degrees of apoptosis are measured 48 hours after the treatments in the case of the SH-SY-5Y strain, and 24 hours after in the case of the SK-N-BE Bep 75 strain, by quantification of the DNA fragment-associated cytoplasmic histones (cell death detection ELISA, Boehringer Mannheim, Germany). The degrees of apoptosis are expressed as amount of oligonucleosomes/$10^5$ cells. Each value corresponds to the mean of 9 experimental points distributed over 3 independent experiments.

The compounds of formula (I) exhibit an inhibitory activity on NGF-induced apoptosis, with $IC_{50}$ values which range from $10^{-6}$ to $10^{-11}$M.

For example, compounds No. 9 and 11 showed an $IC_{50}$ of 0.72 nM and 4.46 nM, respectively.

Thus, the binding of the compounds according to the invention to the $p75^{NTR}$ receptor results, on the one hand, at the biochemical level, in the inhibition of the dimerization of the receptor induced by neurotrophins, or independently of the ligand, and, on the other hand, at the cellular level, in the inhibition of the proapoptotic effect mediated by the $p75^{NTR}$ receptor.

Thus, according to one of the subjects of the present invention, the compounds of formula (I) exhibit a very advantageous activity of inhibition of the dimerization of the $p75^{NTR}$ receptor, independently of its ligand.

The compounds according to the invention can therefore be used for the preparation of medicaments, in particular of medicaments for use in preventing or treating any pathological condition where the $p75^{NTR}$ receptor is involved, more particularly those indicated hereinafter.

The compounds according to the invention can also be used for preventing or treating any pathological condition where the $p75^{NTR}$ receptor is involved, more particularly those indicated hereinafter.

Thus, according to another of its aspects, a subject of the invention is medicaments which comprise a compound of formula (I), or an addition salt of the latter with a pharmaceutically acceptable acid.

Thus, the compounds according to the invention can be used, in humans or in animals, in the treatment or prevention of various $p75^{NTR}$-dependent conditions, such as central and peripheral neurodegenerative diseases, for instance senile dementia, epilepsy, Alzheimer's disease, Parkinson's disease, Huntington's chorea, Down's syndrome, prion diseases, amnesia, schizophrenia, depression, bipolar disorder; amyotrophic lateral sclerosis, multiple sclerosis; cardiovascular conditions, for instance post-ischaemic cardiac damage, cardiomyopathies, myocardial infarction, heart failure, cardiac ischaemia, cerebral infarction; peripheral neuropathies (of diabetic, traumatic or iatrogenic origin); damage to the optic nerve and to the retina (retinal pigment degeneration, glaucoma); retinal ischaemia; macular degeneration; spinal cord traumas and cranial traumas; atherosclerosis; stenoses; cicatrization disorders; alopecia.

The compounds according to the invention may also be used in the treatment of pancreatitis and of hepatic fibrosis.

The compounds according to the invention may also be used in the treatment of cancers, for instance lung cancer, thyroid cancer, pancreatic cancer, prostate cancer, cancer of the small intestine and of the colon, or breast cancer, or in the treatment of tumours, of metastases and of leukaemias.

The compounds according to the invention may also be used in the treatment of respiratory disorders, for instance pulmonary inflammation, allergy, asthma and chronic obstructive pulmonary disease.

The compounds according to the invention may also be used in the treatment of cutaneous pain (in the skin, the subcutaneous tissues and the associated organs), somatic pain, visceral pain (in the circulatory, respiratory, gastrointestinal or urogenital system), and neurological pain.

The compounds according to the invention may be used in the treatment of chronic neuropathic and inflammatory pain, and in the treatment of autoimmune diseases, such as rheumatoid arthritis.

The compounds according to the invention may also be used in the treatment of diseases such as ankylosing spondylarthritis, psoriatic arthritis, or plaque psoriasis.

The compounds according to the invention may also be used in the treatment of bone fractures, or in the treatment or prevention of bone diseases such as osteoporosis.

According to another of its aspects, the present invention relates to pharmaceutical compositions comprising, as active ingredient, a compound according to the invention. These pharmaceutical compositions contain an effective dose of at least one compound according to the invention, or a pharmaceutically acceptable salt of said compound, and also at least one pharmaceutically acceptable excipient.

Said excipients are chosen, according to the pharmaceutical form and the method of administration desired, from the customary excipients which are known to those skilled in the art.

In the pharmaceutical compositions of the present invention for oral, sublingual, subcutaneous, intramuscular, intravenous, topical, local, intratracheal, intranasal, transdermal or rectal administration, the active ingredient of formula (I) above, or salt thereof, may be administered in unit administration form, as a mixture with conventional pharmaceutical excipients, to animals and to human beings for the prevention or treatment of the disorders or of the diseases above.

The suitable unit administration forms comprise oral administration forms such as tablets, hard or soft gel capsules, powders, granules and oral solutions or suspensions, sublingual, buccal, intratracheal, intraocular, intra-auricular and intranasal administration forms, forms for administration by inhalation, topical administration forms, parenteral administration forms, such as transdermal, subcutaneous, intramuscular or intravenous administration forms, rectal administration forms, and implants. For topical application, the compounds according to the invention may be used in creams, gels, ointments or lotions.

By way of example, a unit administration form of a compound according to the invention in tablet form may comprise the following components:

| | |
|---|---|
| Compound according to the invention | 50.0 mg |
| Mannitol | 223.75 mg |
| Sodium croscarmellose | 6.0 mg |
| Maize starch | 15.0 mg |
| Hydroxypropylmethylcellulose | 2.25 mg |
| Magnesium stearate | 3.0 mg |

The dose of active ingredient administered per day may reach 0.01 to 100 mg/kg, as one or more intakes, preferably 0.02 to 50 mg/kg. In general, the daily dose of the compound of the invention will be the lowest effective dose of the compound capable of producing a therapeutic effect.

There may be particular cases where higher or lower dosages are appropriate; such dosages do not depart from the context of the invention. According to the customary practice, the dosage suitable for each patient is determined by the physician according to the method of administration and the weight and response of said patient.

According to another of its aspects, the present invention also relates to a method of treating the pathological conditions indicated above, which comprises the administration, to a patient, of an effective dose of a compound according to the invention, or a pharmaceutically acceptable salt thereof.

What is claimed is:

1. A compound of formula (II):

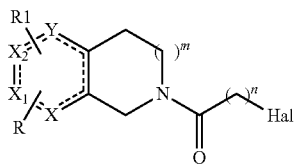

wherein
n represents 1 or 2;
m represents 1;
Y represents a carbon, nitrogen, sulphur or oxygen atom or a single or double bond;
$X_1$ represents a carbon, nitrogen, sulphur or oxygen atom, and X and $X_2$ represent a carbon, nitrogen, or oxygen atom, wherein one or more of X, $X_1$ and $X_2$ is other than a carbon atom;
R and R1, located on any one of the available positions, independently represent a hydrogen atom, a halogen atom, a (C1-C4)alkyl group, a (C1-C4)alkoxy group, a perfluoroalkyl radical, a trifluoromethoxy radical, a cyano, or a COOH, COOalkyl, CONR5R6 or NHCOR5 group;
or R1 represents a group chosen from:

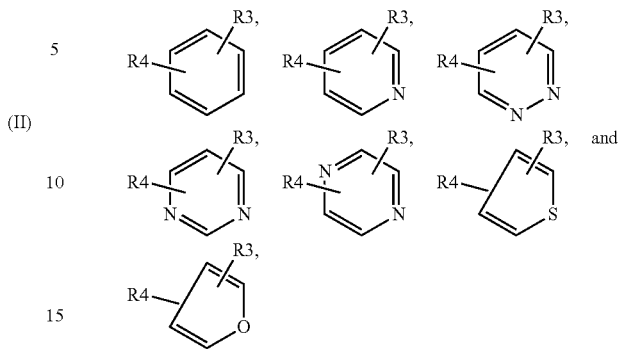

the definition of R remaining unchanged;
R3 and R4, located on any one of the available positions, independently represent a hydrogen atom, a halogen atom, a (C1-C4)alkyl group, a (C1-C4)alkoxy group, a perfluoroalkyl radical, a trifluoromethoxy radical, a cyano, or a COOH, COOalkyl, CONR5R6 or NHCOR5 group;
R5 and R6 represent a hydrogen or a C1-C6 alkyl group;
and Hal represents a halogen atom;
or an acid addition salt thereof.

* * * * *